US011246971B2

(12) United States Patent
Frinak et al.

(10) Patent No.: US 11,246,971 B2
(45) Date of Patent: Feb. 15, 2022

(54) SYSTEM AND METHOD OF MONITORING DISLODGEMENT OF VENOUS NEEDLES IN DIALYSIS PATIENTS

(71) Applicant: HENRY FORD HEALTH SYSTEM, Detroit, MI (US)

(72) Inventors: Stanley Frinak, Farmington Hills, MI (US); Gerard Zasuwa, West Bloomfield, MI (US); Jerry Yee, Beverly Hills, MI (US); Anatole Besarab, Bloomfield Hills, MI (US)

(73) Assignee: Henry Ford Health System, Detroit, MI (US)

( * ) Notice: Subject to any disclaimer, the term of this patent is extended or adjusted under 35 U.S.C. 154(b) by 503 days.

(21) Appl. No.: 16/334,157

(22) PCT Filed: Sep. 19, 2017

(86) PCT No.: PCT/US2017/052146
§ 371 (c)(1),
(2) Date: Mar. 18, 2019

(87) PCT Pub. No.: WO2018/053461
PCT Pub. Date: Mar. 22, 2018

(65) Prior Publication Data
US 2019/0381233 A1 Dec. 19, 2019

Related U.S. Application Data

(60) Provisional application No. 62/396,400, filed on Sep. 19, 2016.

(51) Int. Cl.
*A61M 1/36* (2006.01)
*A61M 5/168* (2006.01)

(52) U.S. Cl.
CPC ...... *A61M 1/3656* (2014.02); *A61M 5/16854* (2013.01); *A61M 1/3641* (2014.02);
(Continued)

(58) Field of Classification Search
CPC .... A61M 1/36; A61M 1/3607; A61M 1/3656; A61M 1/3639; A61M 1/3641;
(Continued)

(56) References Cited

U.S. PATENT DOCUMENTS 3,920,004 A 11/1975 Nakayama
4,303,068 A 12/1981 Zelman
(Continued)

FOREIGN PATENT DOCUMENTS

EP 0240101 A2 10/1987
EP 0311709 A1 4/1989
(Continued)

OTHER PUBLICATIONS

International Search Report and Written Opinion for Application No. PCT/US2017/052146, dated Feb. 9, 2018, 9 pages.
(Continued)

*Primary Examiner* — Philip R Wiest
(74) *Attorney, Agent, or Firm* — Brooks Kushman P.C.

(57) ABSTRACT

A method and a system are provided for detecting a condition indicative of a dislodged needle in a hemodialysis procedure. A venous return pressure for a patient undergoing dialysis is measured. The venous return pressure is analyzed via a controller, and an intravascular blood pressure in proximity to a location of needle insertion into the patient is derived. A lower limit is calculated as a function of the intravascular blood pressure via the controller. An average of the venous return pressure is calculated via the controller during a predetermined time window. The average is compared to the lower limit via the controller, and if the average (Continued)

is within a specified range of the lower limit, the controller determines that a condition indicative of a dislodged needle is present.

26 Claims, 15 Drawing Sheets

(52) U.S. Cl.
CPC ......... *A61M 1/3655* (2013.01); *A61M 1/3661* (2014.02); *A61M 2205/15* (2013.01); *A61M 2205/18* (2013.01); *A61M 2230/30* (2013.01)

(58) Field of Classification Search
CPC .............. A61M 1/3653; A61M 1/3655; A61M 1/3658; A61M 1/3659; A61M 1/3661; A61M 5/16854; A61M 5/16859; A61M 5/16863; A61M 5/16568; A61M 5/16872; A61M 2205/18; A61M 2230/30
See application file for complete search history.

(56) References Cited

U.S. PATENT DOCUMENTS

| | | | |
|---|---|---|---|
| 4,466,804 A | 8/1984 | Hino | |
| 4,524,777 A | 6/1985 | Kisioka et al. | |
| 4,531,941 A | 7/1985 | Zasuwa | |
| 4,677,984 A | 7/1987 | Sramek | |
| 4,710,163 A | 12/1987 | Butterfield | |
| 4,710,164 A | 12/1987 | Levin et al. | |
| 4,735,212 A | 4/1988 | Cohen | |
| 4,828,543 A | 5/1989 | Weiss et al. | |
| 5,453,576 A | 9/1995 | Krivitski | |
| 5,533,511 A | 7/1996 | Kaspari et al. | |
| 5,749,364 A | 5/1998 | Sliwa, Jr. et al. | |
| 5,873,835 A | 2/1999 | Hastings et al. | |
| 6,090,048 A | 7/2000 | Hertz et al. | |
| 6,221,040 B1 | 4/2001 | Kleinekofort | |
| 6,228,033 B1 | 5/2001 | Koobi et al. | |
| 6,371,921 B1 | 4/2002 | Caro et al. | |
| 6,383,158 B1 | 5/2002 | Utterberg et al. | |
| 6,471,872 B2 | 10/2002 | Kitaevich et al. | |
| 6,514,225 B1 | 2/2003 | Utterberg et al. | |
| 6,517,508 B1 | 2/2003 | Utterberg et al. | |
| 6,579,241 B2 | 6/2003 | Roeher | |
| 6,595,942 B2 | 7/2003 | Kleinekofort | |
| 6,623,443 B1 | 9/2003 | Polaschegg | |
| 6,745,630 B2 | 6/2004 | Gross | |
| 6,755,801 B2 | 6/2004 | Utterberg et al. | |
| 7,172,570 B2 | 2/2007 | Cavalcanti et al. | |
| 7,597,666 B2 | 10/2009 | Frinak et al. | |
| 8,348,850 B2 | 1/2013 | Frinak et al. | |
| 2005/0096578 A1 | 5/2005 | Kleinekofort | |
| 2005/0203493 A1 | 9/2005 | Kuroda et al. | |
| 2006/0074369 A1 | 4/2006 | Oishi et al. | |
| 2006/0076169 A1* | 4/2006 | Brendel | A61G 5/045 180/11 |
| 2006/0157408 A1 | 7/2006 | Kuroda et al. | |
| 2006/0272421 A1 | 12/2006 | Frinak et al. | |
| 2007/0016084 A1 | 1/2007 | Denault | |
| 2008/0195021 A1 | 8/2008 | Roger et al. | |
| 2008/0217245 A1 | 9/2008 | Rambod et al. | |
| 2009/0024072 A1 | 1/2009 | Criado et al. | |
| 2009/0171165 A1 | 7/2009 | Izumi | |
| 2010/0022934 A1 | 1/2010 | Hogard | |
| 2010/0073171 A1* | 3/2010 | Frinak | A61M 1/3656 340/573.1 |
| 2015/0246171 A1 | 9/2015 | Wolff et al. | |
| 2015/0246173 A1* | 9/2015 | Steger | A61M 1/3656 604/6.01 |

FOREIGN PATENT DOCUMENTS

| | | |
|---|---|---|
| JP | 2010136841 A | 6/2010 |
| WO | 2010011444 A1 | 1/2010 |
| WO | 2012067585 A1 | 5/2012 |
| WO | 2012175267 A1 | 12/2012 |

OTHER PUBLICATIONS

International Preliminary Report on Patentability for Application No. PCT/US2017/052146, dated Mar. 28, 2019, 6 pages.

Rititsch et al., "Prevalence of Detectable Venous Pressure Drops Expected with Venous Needle Dislodgement", Seminars in Dialysis, vol. 27, No. 5, Sep.-Oct. 2014, pp. 507-511.

Zasuwa et al., "Automated Intravascular Access Pressure Surveillance Reduces Thrombosis Rates", Seminars in Dialysis, 2010, 9 pages.

European Office Action for Application No. 17851750.4, dated Dec. 7, 2020, 6 pages.

Extended European Search Report for Application No. 17851750.4, dated Apr. 14, 2020, 7 pages.

* cited by examiner

Figure 1 Laboratory Schematic for Venous Needle Dislodgment Experimental Testing

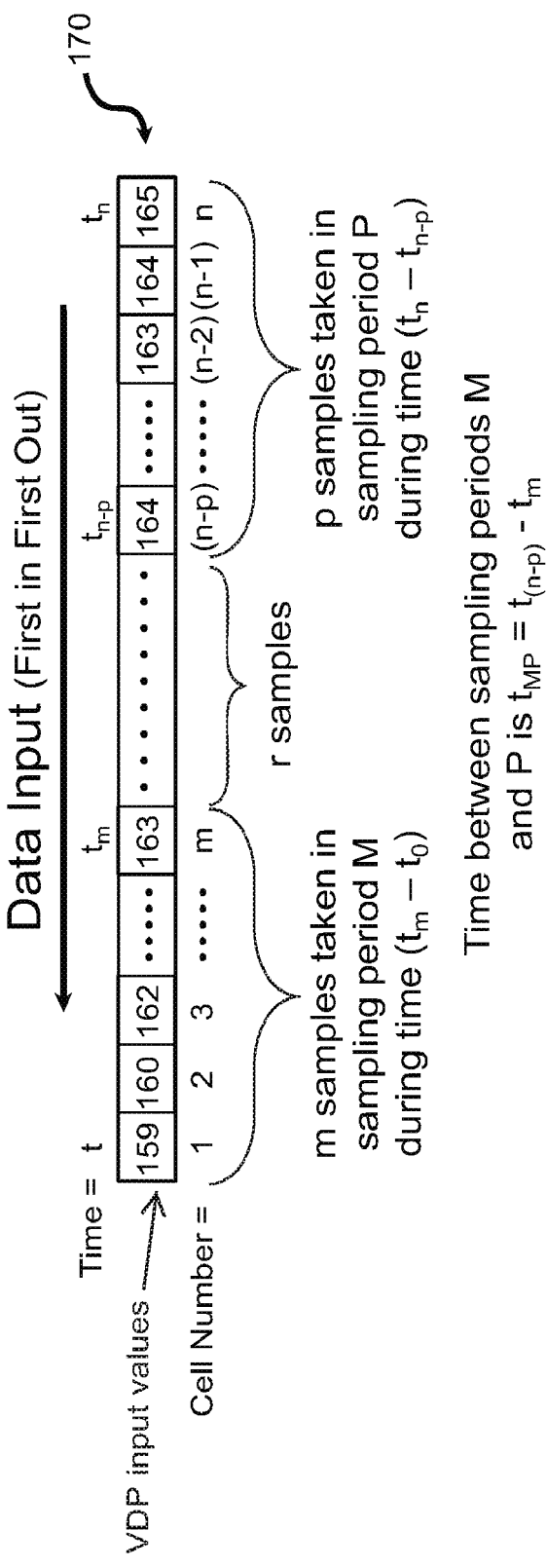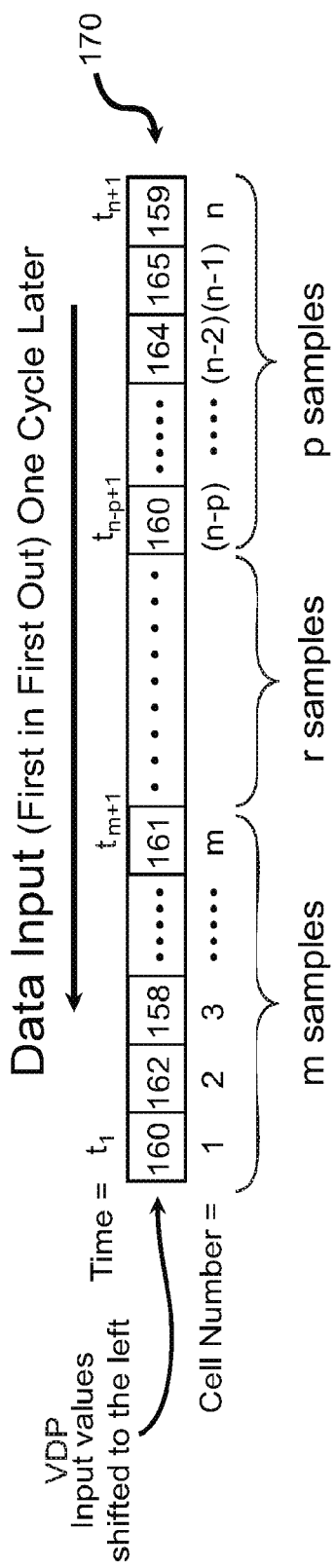

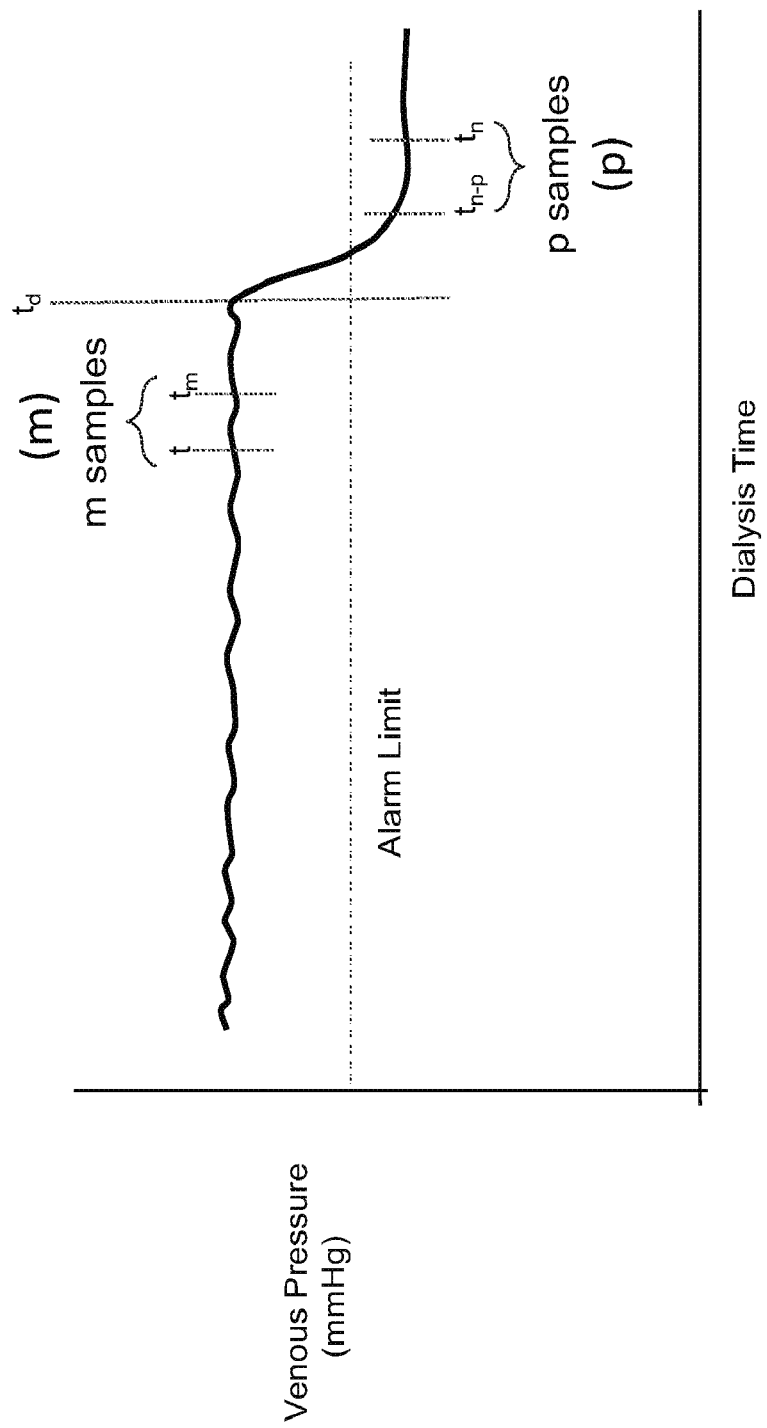

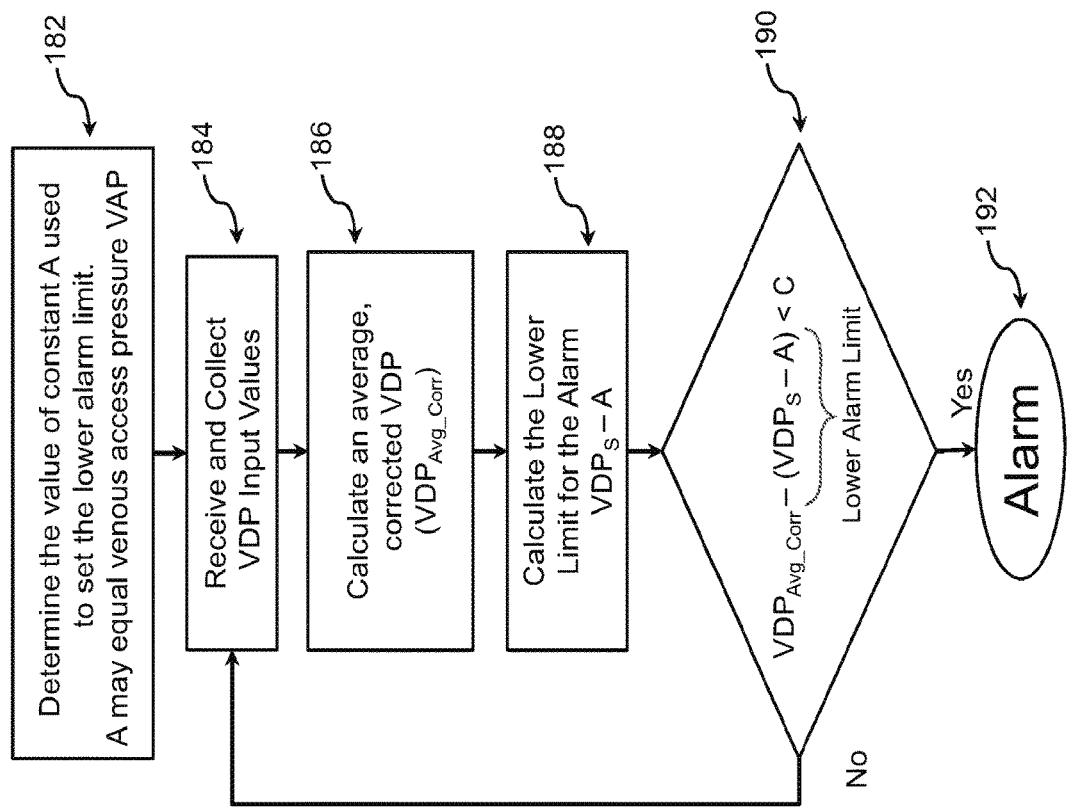

Figure 13  Pressure Measurement Pod with Diaphragm for Use with Medical Fluids

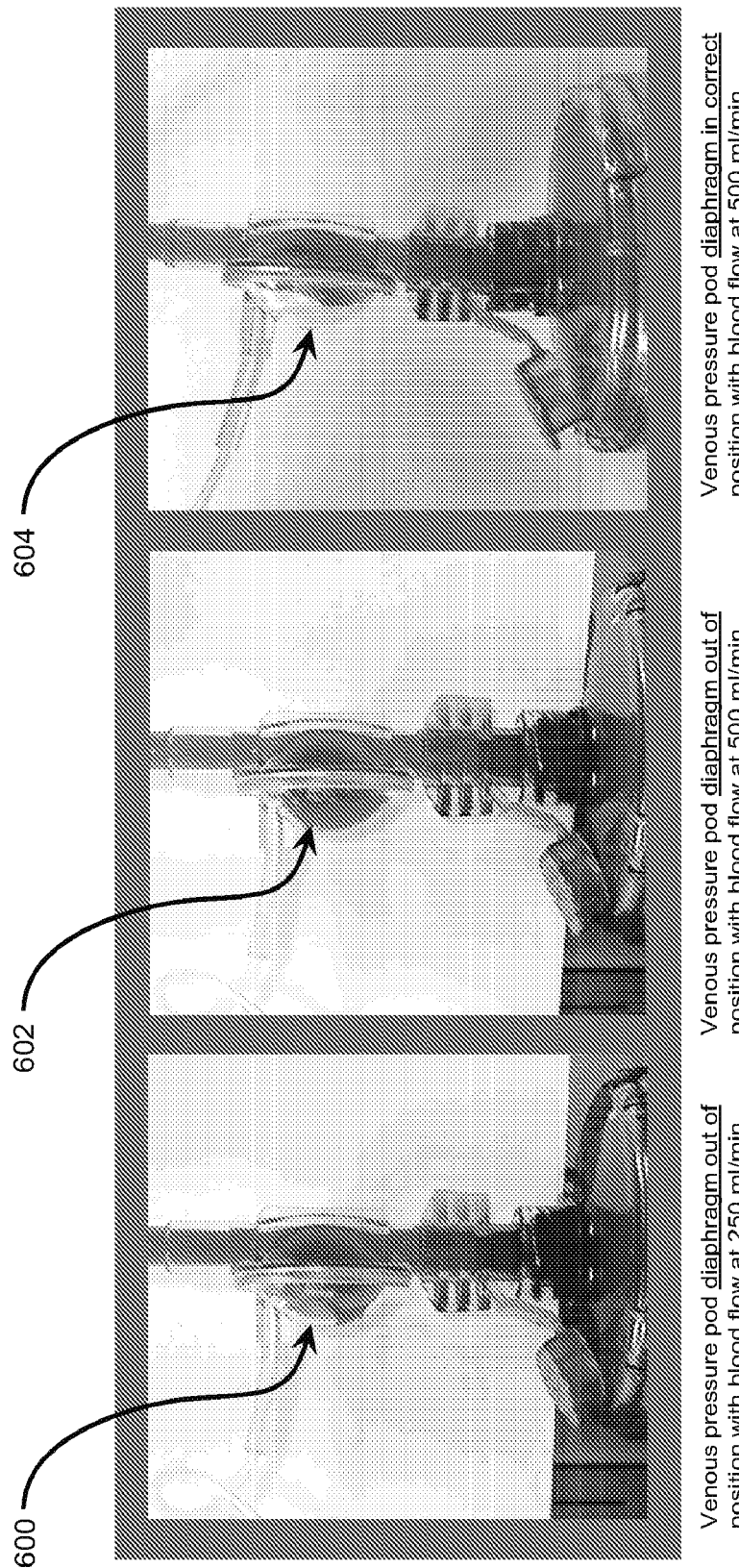
Figure 15  Pressure measurements made with pod diaphragm out of position and in the correct position for different blood flow rates.

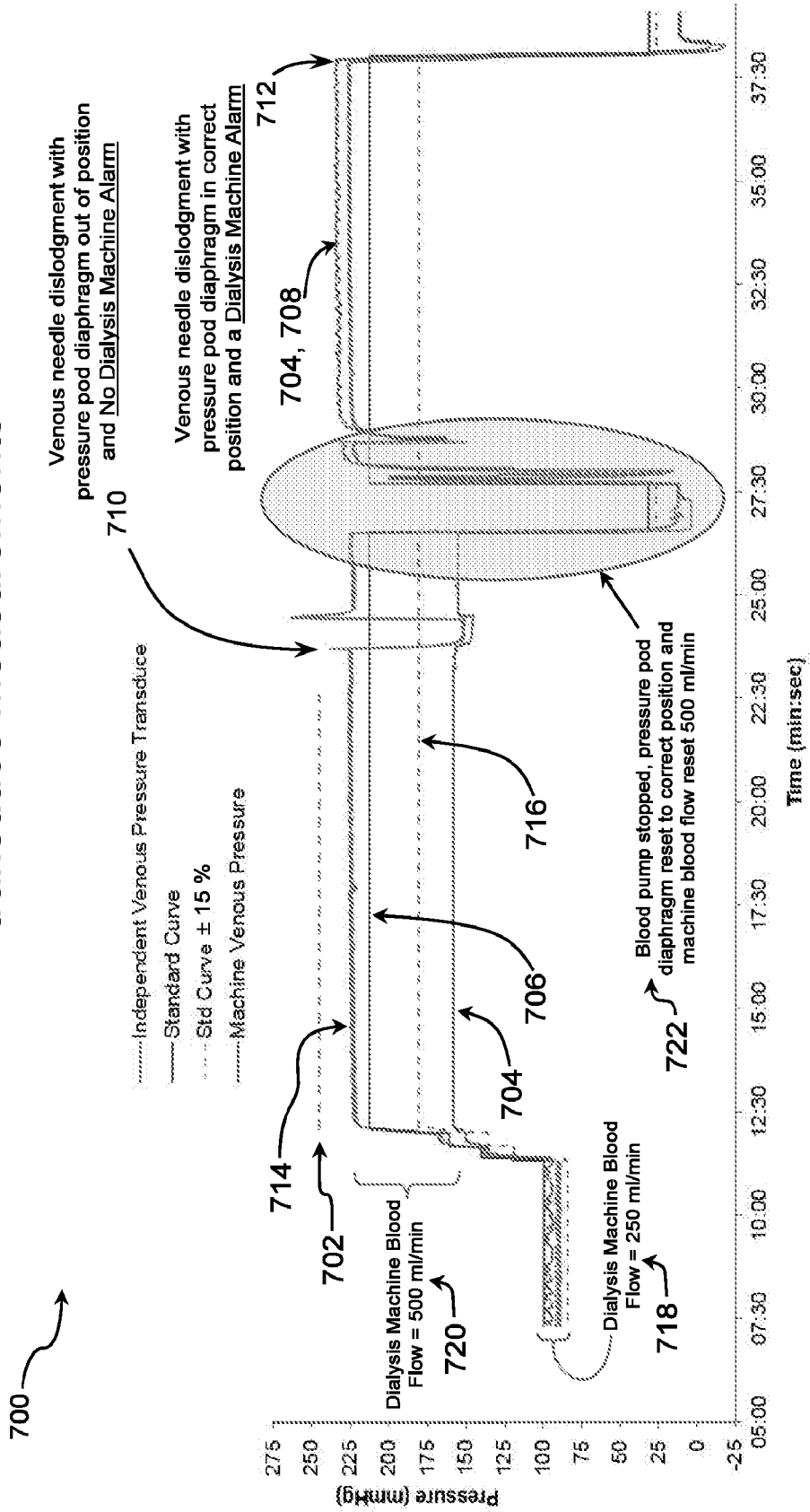

SYSTEM AND METHOD OF MONITORING DISLODGEMENT OF VENOUS NEEDLES IN DIALYSIS PATIENTS

CROSS-REFERENCE TO RELATED APPLICATIONS

This application is the U.S. National Phase of PCT/US2017/052146 filed Sep. 19, 2017, which claims the benefit of U.S. provisional application Ser. No. 62/396,400 filed Sep. 19, 2016, the disclosures of which are hereby incorporated in their entirety by reference herein.

TECHNICAL FIELD

Various embodiments relate to a system and method for monitoring dislodgement of venous needles in dialysis patients.

BACKGROUND

In the field of hemodialysis and other techniques where blood is removed from a patient for processing and then returned, it is important to periodically assess the blood flow rate through an arteriovenous fistula, graft, or catheter to monitor the venous needle position. This is often accomplished by the reading of access pressures through the venous and arterial access needles.

Dialysis is a very complicated procedure that must be carried out by a team of trained professionals who are responsible for delivering safe and effective care to the patient. It can also be self-administered by a patient in their home, but only after the patient has undergone extensive training. There are many ways that complications can arise during a dialysis session. Many of these potential issues are constrained by alarm circuits and other safeguards built into the dialysis machine; however, needle dislodgement or displacement is often undetected or detected after a significant time delay.

SUMMARY

In an embodiment, a method of detecting a condition indicative of a dislodged needle in a hemodialysis procedure is provided. A venous return pressure for a patient undergoing dialysis is measured. The venous return pressure is analyzed via a controller, and an intravascular blood pressure in proximity to a location of needle insertion into the patient is derived. A lower limit is calculated as a function of the intravascular blood pressure via the controller. An average of the venous return pressure is calculated via the controller during a predetermined time window. The average is compared to the lower limit via the controller, and if the average is within a specified range of the lower limit, the controller determines that a condition indicative of a dislodged needle is present.

In another embodiment, a device for detecting a condition indicative of a dislodged needle in a hemodialysis procedure is provided and has a controller. The controller is configured to communicate with a hemodialysis machine. The controller is configured to: (i) receive a signal indicative of a venous return pressure measurement for a patient undergoing dialysis, (ii) analyze the measured venous return pressure and derive an intravascular blood pressure in proximity to a location of needle insertion into the patient, (iii) calculate a lower limit as a function of the intravascular blood pressure, (iv) calculate an average of the venous return pressure during a predetermined time window, (v) compare the average to the lower limit, and if the average is within a specified range of the lower limit, determine that a condition indicative of at least a partially dislodged needle is present, and (vi) provide at least one of a first signal configured to activate an alert to notify medical personnel and a second signal configured to stop a blood pump of the hemodialysis machine.

In yet another embodiment, a method is provided of detecting a condition indicative of a dislodged needle in a medical procedure with a system having an extracorporeal fluid circuit receiving and returning blood to a patient. A first fluid pressure is measured in the circuit upstream of a location of needle insertion into the patient. The first fluid pressure is analyzed via a controller, and a second fluid pressure in proximity to the location of needle insertion into the patient is derived. A lower limit is calculated via the controller as a function of the second fluid pressure. An average of the first fluid pressure over a predetermined time interval is calculated via the controller. If the average is within a specified range of the lower limit, the controller determines that a condition indicative of a dislodged needle is present.

BRIEF DESCRIPTION OF THE DRAWINGS

FIG. 3 is a matrix used by the method as implemented by a controller at time (t);

FIG. 4 is a matrix as used by the method as implemented by a controller at time (t+1);

FIG. 6 is a graph illustrating the change in average VDP during a needle dislodgement;

FIG. 7 is a flow chart illustrating a method for monitoring for needle dislodgement according to another embodiment;

FIG. 15 illustrates the device of FIG. 13 under three different operating conditions and configurations; the figure on the left and in the center show fluid pressures of approximately 100 mmHg and 220 mmHg where the diaphragm is out of position i.e. filled with excess fluid. The figure on the right shows the diaphragm in the correct position at a fluid pressure of approximately 220 mmHg; and FIG. 16 plots various pressures with time as measured by the device of FIG. 13, measured by an independent pressure transducer, and calculated by a controller under various conditions including during a sham dialysis procedure mimicking a venous needle dislodgement.

DETAILED DESCRIPTION

Figure 1:
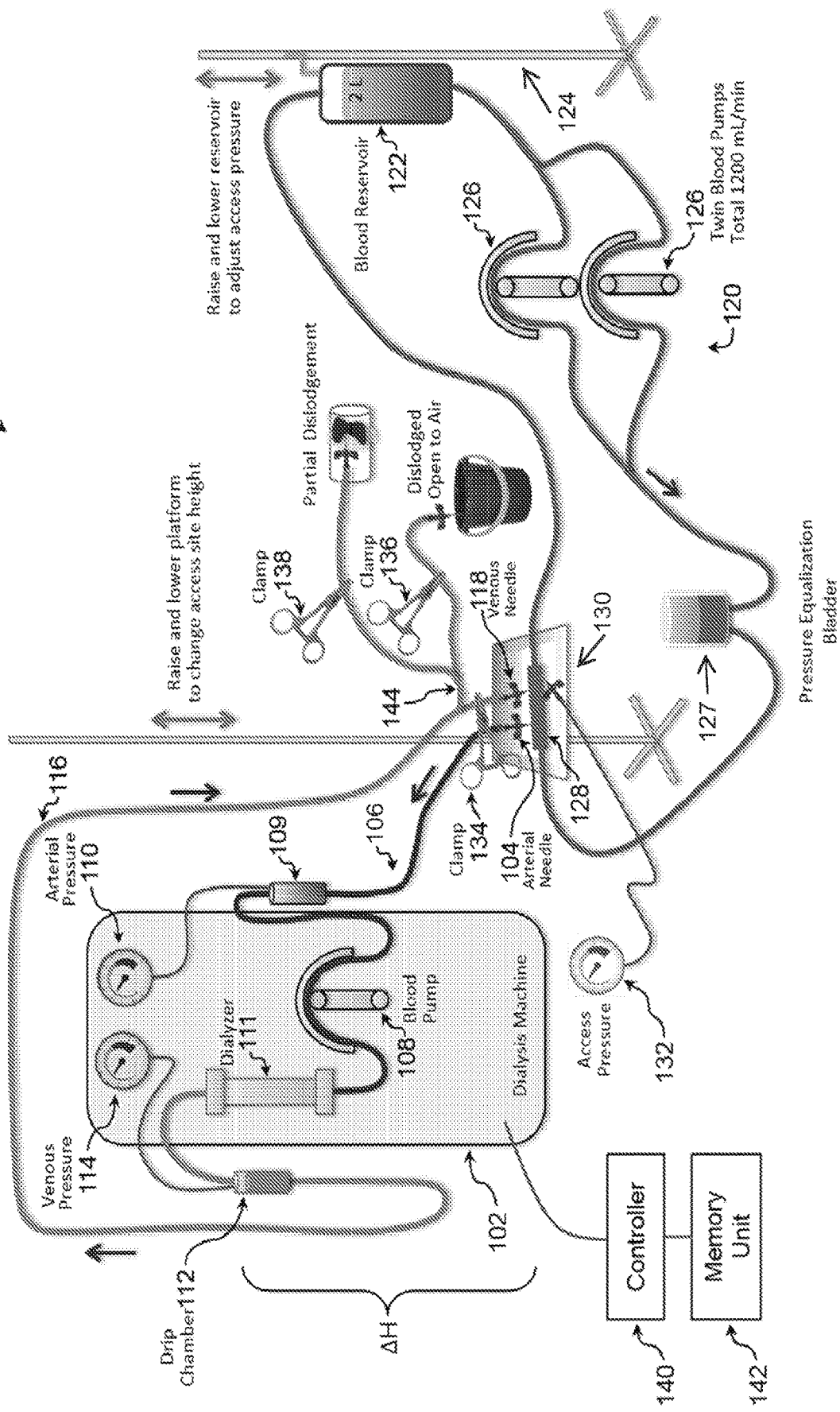
FIG. 1 illustrates a schematic of a dialysis circuit for use in determining venous needle dislodgement according to an embodiment.

As required, detailed embodiments of the present disclosure are provided herein; however, it is to be understood that the disclosed embodiments are merely exemplary and may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present disclosure.

Generally, according to an aspect of the present disclosure, a detection device and method are provided for detecting variations in intravascular pressure that indicate irregular blood flow, i.e. when a needle of a hemodialysis device has become dislodged from a patient. The device includes an analyzer for automatically analyzing intravascular pressure upstream of the suspected location of irregular blood flow and comparing the intravascular pressure to a standard.

Hemodialysis machines utilize two needles, one to remove blood from the patient (arterial) and one to put the dialyzed blood back into the patient (venous needle). The venous needle can become dislodged or displaced from the patient, such as accidentally pulled out of the access, which then allows the blood being pumped back into the patient to run onto the floor. Because of the relatively high blood flows of the dialysis machines (300 to 500 ml of blood per minute), if this dislodgement goes unnoticed the patient can bleed to death in a short amount of time. For example, an average male patient can lose 40% of their blood supply in eight minutes. Even in a hospital or clinical setting, dislodgement can sometimes occur without any visual detection by a medical staff because a blanket can cover the bloodlines. This issue is even more of a concern when a patient is dialyzed overnight. This can be more convenient for patients who do not want to spend the day in the hospital, with the hemodialysis procedure being performed while they are asleep. However, overnight dialysis poses even more of a risk that the dislodgement of the venous line needle during the procedure will go unnoticed. For example, if the patient rolls over during sleep or otherwise significantly moves in the hospital bed, this can cause needle dislodgement. A large quantity of blood can be lost and death can result in many cases. It has been estimated that between 40 and 136 patients die each year in the US due to losing sufficient blood because of needle displacement.

A current method of detecting dislodgement of a needle is visual monitoring by staff that must instruct the patient not to cover venous lines with a blanket. While many hemodialysis machines do include some sort of alarm to indicate pressure changes in the venous and arterial bloodlines, dislodgement of needles generally do not trigger an alarm, so the dislodgment is often not detected until too late. The reason for this is that small gauge needles that are used to minimize pain to patients create back-pressures that continue to be detected by the machine when the needle is dislodged. This sufficient back-pressure created in the tubing and needle masks the pressure drop at the tip of the needle if it becomes dislodged, such that the drop in the pressure caused by the removal of the needle from the arm, and hence the loss of the pressure required to push the blood into the patient's arm, is not high enough to show a significant change in the pressure as measured by the venous drip chamber transducer, especially if the range of alarm is not set correctly on the machine. Thus, sufficient pressure remains in the circuit between the tubing and the needle so that the measured venous drip pressure does not drop significantly, and no alarm is set off. There is a need for a more reliable method of detecting dislodgement of venous needles from a patient as well as an alarm system to turn off the blood pump on the dialysis machine and alert medical personnel in time to save a patient's life.

Currently, venous pressure alarm systems set alarm limits above and below the current venous pressure. For example, on a Fresenius 2008H machine, there are user-selected upper and lower limits that may be set at ±100, ±80 or ±60 relative to the current venous pressure. A further modification of this alarm system allows for an asymmetric limit of −20, −25 or −35 mmHg to be selected for the lower limit in place of the prior lower limit. The alarm algorithm spreads the limits to ±100, ±80 or ±60 when the machine blood flow rate is changed, waits for one minute for the venous pressure to stabilize, and then sets the lower alarm limit to the selected value of 20, 25 or 35 mmHg. Once the alarm limits are selected, the current venous pressure is allowed to drift within the selected alarm limits. An issue may arise with this alarm system as the current venous pressure can drift upward, away from the selected lower limit, for example, due to fluid removal from the blood during the dialysis procedure. In one example, a dialysis machine set to a blood flow of 400 ml/min creates a venous return pressure of 150 mmHg, and initially the venous pressure limits are set to be ±80 and one minute later the asymmetric lower limit is set to −25 mmHg. In this case, the upper and lower venous limits are 230 and 70 mmHg when the blood flow is first set to 400 ml/min, and one minute later the upper and lower limits are set to be 230 and 125 mmHg. If the current venous pressure drifts up to 35 mmHg during the next twenty minutes to a value of 185 mmHg, the lower limit is now 60 mmHg away from the set lower limit of 125 mmHg. Under these conditions if the venous needles is dislodged the venous pressure will have to drop 60 mmHg before the venous alarm is activated, not the expected drop of only 25 mmHg. It is also possible under certain treatment conditions for current venous pressure to drift downwards, thereby reducing the pressure drop needed to activate the venous alarm and creating the possibility for a nuisance alarm.

According to an aspect of the present disclosure, a method is provided for detecting a dislodged needle in a hemodialysis procedure by measuring venous return pressure, e.g. a venous drip chamber pressure or a measurement of the pressure required to return blood in a patient, analyzing the venous drip pressure and monitoring for a change in an average venous intravascular blood pressure or intraccess blood pressure at the location of needle placement in the patient to determine that something is wrong with the venous needle and should be investigated. According to another aspect of the present invention, a method is provided of shutting down the dialysis machine and alerting medical personnel of a dislodged needle in a hemodialysis procedure.

The "detection device" as disclosed herein is intended to include, but is not limited to, any device that is able to detect variations in intravascular pressure that indicate irregular blood flow. In one embodiment, the intravascular pressure is venous pressure that is upstream of the suspected area or location of a blood flow restriction. An example of such a device is a hemodialysis machine. The device may incorporate one or more pressure sensors.

The "analyzer device" as used herein is intended to include a device that is capable of automatically analyzing the intravascular pressure. Such an analyzer device may be computer-driven. For example, the analyzer can include a device that is associated with a hemodialysis machine, such that it automatically assesses venous drip chamber pressure during hemodialysis and correlates this with vascular pressure. An equation is used that sets an alert based on irregular blood flow due to low pressure inside a blood access site. In one embodiment, this equation is an algorithm that uses the difference of an average venous return pressure (or venous drip pressure) at a first time and another average venous return pressure (or venous drip pressure) at a second time.

The term "variation" is intended to include an increase or decrease in the derived intravascular pressure. Any deviation from the standard can be indicative of a problem. Depending upon whether there is an increase or decrease in intravascular pressure, the detection of the deviation helps determine what the problem is at the access site.

The term "communication device" as used herein is intended to include a device operably connected to the detecting device for communicating a warning when the detecting device indicates an irregularity of blood pressure of at least two uses of said device. The communicating device can be selected from, but is not limited to, electronic communications, a facsimile, a telephone, a cable modem, a T1 connection, a wireless connection, and a cellular network connection.

The term "algorithm" as used herein is intended to encompass any computation or method that enables an individual to ascertain the information necessary for detecting irregular intravascular pressure. In one embodiment, the algorithm is implemented by the analyzer device, or is computer driven. The algorithm can be used as part of an integrated circuit. This circuit enables the algorithm to be more easily incorporated into a detection device such as a dialysis machine. The circuit may be created using technology known to those with skill in the art.

It is recognized that any circuit or other electrical device disclosed herein may include any number of microprocessors, integrated circuits, memory devices (e.g., FLASH, random access memory (RAM), read only memory (ROM), electrically programmable read only memory (EPROM), electrically erasable programmable read only memory (EEPROM), or other suitable variants thereof) and software which co-act with one another to perform operation(s) disclosed herein. In addition, any one or more of the electrical devices as disclosed herein may be configured to execute a computer-program that is embodied in a non-transitory computer readable medium that is programmed to perform any number of the functions as disclosed herein.

The method in accordance with the present invention may be practiced with the following device or system. The device includes a detection device for detecting irregular intravascular pressure. The device has an analyzer for automatically monitoring intravascular pressure upstream of the suspected location of irregular blood flow, and for comparing intravascular pressure to a standard, whereby variation in the intravascular pressure may be indicative of irregular blood flow. As disclosed above, the device may be affixed to a hemodialysis machine; however, the device can be affixed to any other device with blood flow. The analyzer is a computer-driven device and may include an algorithm that analyzes intravascular pressure, hemodialysis venous access pressure, and blood pump flow data to monitor for conditions indicative of needle dislodgement in a patient during a dialysis treatment. In other examples, the method and device may be implemented to monitor for conditions indicative of needle dislodgement in a patient during another treatment.

More specifically, the present invention provides for a method of detecting a dislodged needle in a hemodialysis procedure by measuring venous return pressure (or venous drip chamber pressure) in a patient, analyzing the venous return pressure and deriving intravascular blood pressure at a location of the venous needle insertion into the patient, comparing the derived intravascular blood pressure to a standard developed from prior calculations during that particular session, and repeating the measuring, analyzing and deriving, and comparing steps to determine if the derived intravascular blood pressure is deviating from the standard, which may indicated that a needle has been dislodged in the hemodialysis procedure.

The venous return pressure is the pressure that is actually measured in the extracorporeal circuit (outside the body), and is further described below. The venous return pressure is also referred to as a venous drip chamber pressure (VDP) or venous drip pressure herein, although a pressure pod or other device may be used in place of a drip chamber in various embodiments according to the present disclosure. The intravascular blood pressure is calculated by analyzing the venous drip pressure and the deriving venous access pressure (VAP) in proximity of a location of venous needle's point of access on the body. These steps are further described below. The derived intravascular blood pressure (VAP) is compared to a standard based on prior measurements of VAP during the session for the patient as further described below. Each of the measuring, analyzing and deriving, and comparing steps may be repeated multiple times during the session when the medical device is in use, for example, in a continuous process at specified time intervals. It may be advantageous from a safety standpoint, as well as monitoring accuracy standpoint, to make these measurements frequently. The device method or algorithm may also or alternatively use a directly measured VAP compared to a standard, with the VAP measured directly by stopping the extracorporeal blood pump, measuring the venous drip chamber pressure, and making a correction for a difference in height between the level of venous drip chamber pressure measurement site and the level of the tip of the venous needle.

Once the intravascular pressure (VAP) has been determined to deviate sufficiently from the standard, possibly indicating that the needle has become dislodged, an alarm circuit may be activated that then communicates via a communication device a command to alert the medical staff and/or automatically turn off the blood pump of the hemodialysis machine, so that the patient does not continue to lose blood.

The device may include an alarm that is activated and alerts medical personnel to a problem with the patient. The alarm may provide a warning indicating that the patient's needle may have come out of the access, i.e. became dislodged. Thus, the difference in averaged venous drip chamber pressures is equal to or close to venous drip chamber at zero access pressure for an alarm to occur. Currently, dialysis machines are limited in their ability to detect an opening of the venous return line and incidents of severe bleeding have been reported when the venous needle has come out of the access site during dialysis. By detecting a drop in the intravascular pressure of the patient, an alarm can be activated on the detecting device that stops the dialysis machine and/or alerts medical personnel to the patient's condition so that the needle can be replaced and the patient can be saved from unnecessary blood loss. The alarm may also be used to wake up the patient if asleep so that the patient can alert medical personnel, and can include a vibrating portion attached to the patient to assist in waking up or alerting the patient as well as an audible portion.

The algorithm according to an aspect of the present invention determines a condition indicating that the actual vascular pressure is zero. Generally, the actual pressure as seen at the tip of the needle may be calculated by removing the pressure caused by the needle and tubing ($VDP_0$) from the measured VDP, which leaves VAP. By building the algorithm into the dialysis machine so that a specified lower limit for VAP (e.g. 5 mmHg, 0 mmHg or another selected limit) is calculated often, an alarm can be sounded and the dialysis machine pump stopped when a condition exists that indicated that VAP has dropped to zero or near zero, thus indicating that the venous needle probably has dislodged. This alarm determination can then a) turn off the machine so that the patient does not lose more blood, and b) sound an alarm to notify either the medical staff or the home care patient that a problem exists.

The algorithm in accordance with the present invention can be utilized as an alarm system in any device that transports blood from a patient to an extracorporeal circuit and returns the blood to the patient. The algorithm determines the pressure at the point of insertion of the blood into the body based on a pressure reading in the extracorporeal blood circuit along with the rate of fluid flow through the device, the physical properties of the fluid transported through the device and a determination of the pressure inherent in the external circuit beginning from the pressure measuring device to the end of the needle at the point of insertion into the body. The algorithm allows the alarm level to vary with the rate of fluid flow through the device. The present device can be utilized as an alarm in plasmapheresis, heart lung machines and any extracorporeal blood treatment or infusion technology circuits. Alarm systems based on the present device are not limited to medical applications but can be developed for any fluid transporting device. Alarm levels can be set at any pressure value that provides safe operation of the device.

The alarm can be a wireless alarm or a hardwired alarm. More specifically, a wireless alarm can send wireless signals to a handheld monitor/device that is carried by medical personnel or to a central monitoring area, such as by the Internet or through communication mechanisms that include, but are not limited to electronic communications, facsimile, telephone, cable modem, and T1 connection. A hardwired alarm can send signals to any device that is in electrical connection with the detecting device of the present invention, such as a central monitoring area. The alarm can also be an audible warning or other similar signal that sends a command to the medical device (such as turn off) and/or wakes up the patient and alerts medical personnel.

Thus, by performing the method according to the present disclosure, if a needle should become dislodged by the patient's movement during sleep or otherwise, the patient's life can be saved by turning off the machine and alerting medical personnel in time.

The invention further provides for a method of alerting medical personnel of a dislodged needle in a hemodialysis procedure by detecting a drop in intravascular pressure derived from measured venous drip pressure, detecting a dislodged needle, and alerting medical personnel of the dislodged needle. Each of the steps of this method is described above.

The detection device can be used to monitor any type of patient blood access site for increased blood pressure and subsequently reduced blood flow. The types of blood access sites that can be monitored include, but are not limited to, fistulas, grafts, catheters, or any type of permanent blood access port. In catheters and permanent blood access ports the plastic materials used to construct the devices become coated with layers of protein and fibrous substances that reduce the internal diameter of the blood pathway or these devices may induce the formation of a vascular stenosis downstream of the implantation site. Any reduction in internal diameter of the blood pathway that results in an increase in pressure upstream of the catheter or permanent blood access port can be detected by the algorithm in the present device and a warning can be issued once an appropriate alarm level is exceeded.

Additionally, the present disclosure can be utilized to describe the relationship between blood flow, pressure, and hematocrit in any type of system that removes blood from a patient and returns the same blood to the patient. Thus, it can be used in conjunction with a heart-lung machine to determine alarm parameters for blood withdrawal and reinfusion.

During hemodialysis, blood is drawn from the vascular access through the arterial needle by the hemodialysis machine blood pump. After passage through the dialyzer, the blood traverses the venous drip chamber and returns to the access through the venous needle. The pressure required to infuse blood back into the access through the venous tubing and access needle and to overcome the pressure within the access is recorded as the venous drip chamber pressure (VDP). One component of VDP is the access pressure at the venous needle site, hereafter, termed "venous access pressure" (VAP). Another component of VDP is the combined pressure required to overcome the resistance to flow through the tubing distal to the drip chamber (low) and through the venous return needle (high). VDP is also a function of needle size, tubing length and blood viscosity, represented by hematocrit. If the venous pressure within an access at the needle site is 0 mmHg, VDP can be defined as $VDP_0$, i.e., the venous drip chamber pressure when the access pressure is zero. Consequently, $VDP_0$ can be calculated for a given hemodialysis machine, tubing set, and needle size when the blood flow rate and hematocrit are measured. Once $VDP_0$ is determined, VAP can be calculated from the measured VDP.

$$VAP = VDP - VDP_0 \quad \text{Equation (1)}$$

The data that yields the determination of $VDP_0$ is contained within a central database repository that holds dialysis laboratory data and parameters acquired from hemodialysis machines that directly communicate with computers in the dialysis units. The algorithm utilizes an empirical formula to calculate VAP from a dynamic measurement of VDP obtained at treatment and digitally or otherwise recorded.

Analysis of the data for the hemodialysis machine circuit yielded the following second order polynomial equation, henceforth referred to as Equation (2):

$$VDP_0 = 0.00042*Qb^2 + (0.62116*Hct^2 + 0.01203*Hct + 0.12754)Qb - 17.32509 \quad \text{Equation (2)}$$

In Equation (2), Qb is the hemodialysis blood pump flow rate, and Hct is the hematocrit. Equation (2) can be used to calculate $VDP_0$ for any Qb at known Hct. For example, at Qb=500 ml/min and Hct 18.2%, $VDP_0$ is 163 mmHg and increases to 200 mmHg when Hct=38.4%. VAP can be calculated from VDP recorded during hemodialysis by Equation (1) and VAP is calculated by Equation (1) using the $VDP_0$ calculated in Equation (2). At Hct=38.4% and Qb=500 ml/min, Equation (2) yields $VDP_0$=200 mmHg. If the hemodialysis machine measures a value of VDP=265 mmHg, the calculated VAP=265−200=65 mmHg using Equation (1). In the case where blood flow (Qb) is equal to zero in Equation (2), the following occurs:

$$VDP_0=0+0-17.32509=-17.32509$$

Venous access pressure (VAP) is then calculated by inserting the above value for $VDP_0$ at Qb=0 into Equation (1) as follows:

$$VAP=VDP-VDP_0=VDP-(-17.32509)=VDP+17.32509$$

The constant (−17.32509) may be determined by the dialysis machine type and the level of the patient's access site.

Venous access pressure (VAP) may be calculated according to another example under static conditions with the blood pump on the dialysis machine stopped. The effect of flow resistance due to the venous tubing and the dialysis needle is eliminated. Under static conditions, a static venous access pressure ($VAP_{static}$) may be measured directly if the height difference (ΔH) between the venous needle and the venous pressure measurement site on the dialysis machine is known. Equation (3) below provides $VDP_{static}$, where the static venous drip chamber pressure is measured ($VDP_{static}$), the average density of blood ($D_{blood}$)=1.050 g/cm$^3$ for a hematocrit ranging from 25% to 40% is used, and the density of mercury 13.595 g/cm$^3$:

$$VAP=VAP_{static}=VDP_{static}+(D_{blood}/D_{mercury})(\Delta H)=VDP_{static}+0.77\,\Delta H \quad \text{Equation (3)}$$

where the term 0.77ΔH is the hydrostatic pressure caused by the height difference ΔH in centimeters and $VAP_{static}$ is given in mmHg. ["Reference Prevalence of detectable venous pressure drops expected with venous needle dislodgement," Ribitsch W, Schilcher G, Hafner-Giessauf H, Krisper P, Horina J H, Rosenkranz A R, Schneditz D, *Semin Dial.* 2014 September-October; 27(5):507-11. doi: 10.1111/sdi.12169. Epub 2013 Dec. 17.]

Clinical studies have shown that the venous drip chamber pressure recorded by the machine and corrected for the height difference between the drip chamber transducer and the patient's access gives an accurate value for venous access pressure. The algorithm can therefore be incorporated into the dialysis machine. The dialysis machine therefore automatically records the readings. Additionally, a sensor can be placed on the hemodialysis machine to determine the height difference between the venous drip chamber transducer and the level of the patient's access site. Additional details of $VDP_0$ may be found in U.S. Pat. No. 8,348,850 B2 issued on Jan. 8, 2013, and incorporated by reference in its entirety herein.

The algorithm relies on a nonlinear regression formula to calculate $VDP_0$ for specific hemodialysis blood tubing set and access needle when the patient's hemodialysis blood pump flow (Qb) and hematocrit are known. The formula was developed from data analysis obtained during in vitro sham hemodialysis.

FIG. 1 illustrates a diagram of the experimental hemodialysis system 100. A dialysis machine (Fresenius 2008H, Lexington, Mass., U.S.A.) 102 blood pump 108 is provided and has an arterial needle 104 connected to tubing 106. A pump 108 in the dialysis machine 102 operates to provide suction at the arterial needle 104 and draws blood into the machine 102. An arterial pressure sensor 110 is provided to measure the pressure in the machine 102 upstream of the pump 108, for example, at an arterial drip chamber 109.

From the pump 108, blood flows through a dialyzer 111 and into a venous drip chamber 112. A venous drip chamber pressure sensor 114 is provided to measure the venous drip pressure, or VDP, in the chamber 112. From the chamber 112, blood flows through tubing 116 to a venous needle 118.

A fluid circuit 120 is provided to simulate a patient undergoing a hemodialysis treatment. The fluid circuit 120 has a reservoir 122 containing blood or another fluid. The reservoir 122 height may be adjusted during testing, for example, using a height adjustable stand 124 or the like, to vary the pressure within the circuit 120. As the height of the reservoir 122 compared to the access 128 is increased, the fluid pressure within the circuit 120 is also increased.

At least one pump 126 is provided in the circuit 120 to circulate blood flow. In the present example, two pumps 126 are used and are operated out of phase from one another to reduce pressure pulsations in the fluid caused by the pumping action. The pumps 126 may be set at the same flow rate, or at different flow rates compared to one another in an attempt to minimize pressure pulsations and fluctuations in the circuit 120 caused by the pumps, e.g. hydraulic pump noise. A fluid accumulator 127 or other device may be included in the circuit 120 to further reduce hydraulic noise and associated pressure fluctuations.

The pumps 126 provide fluid flow to an access 128. In one example, as shown, the access 128 is a sham access as used for experimental testing and validation. The access 128 may be a section of tubing that simulates an arteriovenous graft or arteriovenous fistula in a patient. The access 128 height may be adjusted during testing, for example, using a height adjustable stand 130 or the like, to simulate different patient heights relative to the machine 102. Note that as the height of the access 128 is adjusted, the overall fluid pressure in the circuit 120 may vary if the height of the reservoir 122 is unchanged. A pressure sensor 132 may be provided in the access 128, for example, downstream of the venous needle 118. The pressure sensor 132 measures the pressure in the fluid circuit 120 at the access 128, and provides the experimental equivalent of venous access pressure (VAP). The VAP measured by the sensor 132 may be used to configure the fluid circuit 120 for experimental testing and validation; however, the measured VAP is not used in the algorithm or method for monitoring for a needle dislodgement.

A controller or computer 140 is in communication with or connected to the dialysis machine 102, and may additionally include or be connected to a memory unit 142. The controller 140 is configured to implement the algorithm or method according to the present disclosure to monitor for venous needle dislodgement. The controller 140 and memory unit 142 may provide at least in part the detection device and/or the analyzer device as previously described. In other examples, the controller 140 and memory unit 142 may be integrated into the electronics of the machine 102. The controller 140 may receive signals indicative of the arterial pressure from sensor 110, the VDP chamber pressure from sensor 114, and the flow rate or pump speed of the pump 108 of the machine 102.

During hemodialysis, blood is drawn from the vascular access 128 through the arterial needle 104 by the hemodialysis machine 102 blood pump 108. After passage through the dialyzer 111, the blood traverses the venous drip chamber 112 and returns to the access 128 through the venous needle 118. The pressure required to infuse blood back into the access 128 through the venous tubing 116 and access needle 118 and to overcome the pressure within the access 128 is recorded by sensor 114 as the venous drip chamber pressure (VDP). One component of VDP is the access pressure at the venous needle 118 site (hereafter, termed "venous access pressure" (VAP)). Another component of VDP is the combined pressure required to overcome the resistance to flow through the tubing 116 distal to the drip chamber 112 (low) and through the venous return needle 118 (high). VDP is also a function of needle 118 size, tubing length and blood viscosity, represented by hematocrit. If the venous pressure within an access at the needle 118 site is zero mmHg, VDP can be defined as $VDP_0$, i.e., the venous drip chamber pressure 114 when the access pressure is zero. Consequently, $VDP_0$ can be calculated for a given hemodialysis machine, tubing set, and needle size when the blood flow rate and hematocrit are measured, for example, using Equation (2) above. Once $VDP_0$ is determined, VAP can be calculated from the measured VDP.

The dialysis machine 102 and blood pump 108 was calibrated prior to experiments using the standard maintenance procedure. The reservoir 122 is filled with 500 ml of human whole blood obtained from the hospital blood bank. The blood pumps 126 transport blood from a reservoir 122 through the artificial access site 128 and back to the reservoir 122. The dialysis machine blood pump 108 transports blood from the access site 128 through the dialyzer 111 and the venous drip chamber 112 and then to a 15 gauge, 1-inch back-eye access needle 118. The venous access needle 118 is inserted into a section of large-bore tubing 128 that simulates a patient access. The access needle 118 is positioned at a height (ΔH) that is 17 cm below the venous drip chamber 112 transducer to simulate the average location of a vascular access relative to the transducer during a typical hemodialysis treatment. The pressure inside the access site 128 is set to zero mmHg by adjusting the height of the blood reservoir 122 while monitoring the access pressure using an independent transducer 132 with a fluid path connected directly into the access site 128. The drip chamber transducer 114 monitors the pressure created by the blood flowing through the circuit of the machine 102. $VDP_0$ readings are obtained directly from the hemodialysis machine 102. A sample of blood is obtained for hematocrit determination, for example, from the reservoir 122. $VDP_0$ may be recorded as the flow rate (Qb) is increased from 0 to 600 ml/mm in 50 ml/mm increments, although other increments are also contemplated. The blood is then diluted with matched human plasma to lower hematocrit by approximately 4%, although other hematocrit reductions via dilution are also contemplated. Blood is permitted to circulate at 500 ml/mm for five minutes or another time interval to ensure uniform mixing with the additional plasma before the next sample is obtained for hematocrit measurement. $VDP_0$ measurements are repeated for Qb from 0 to 600 ml/mm. The circulated blood is diluted five times, which reduces the original hematocrit by approximately 20 percentage points. $VDP_0$ measurements were conducted at each of the five dilutions. Data from the $VDP_0$ measurements is used in a multiple nonlinear regression analysis program to calculate coefficients for equation (2) the equation for determining $VDP_0$. In practice once $VDP_0$ is determined for a specific dialysis machine, blood tubing set and type of access needles, $VDP_0$ can be used to calculate VAP using equation (1) without stopping the dialysis machine blood pump 108. If the equation for $VDP_0$ is present in the dialysis machine computer 140 and memory 142 and the dialysis machine 102 also utilizes a device to continuously monitor the hematocrit of the blood in the dialysis circuit, the value of the VAP can be updated continuously throughout the treatment using the updated value of $VDP_0$.

The value of VAP can now be determined using a method or algorithm that establishes a lower alarm limit for the current VDP that is being measured continuously by the dialysis machine 102. The algorithm determines a condition indicative of needle 118 dislodgement in a patient during a hemodialysis treatment. For the experimental hemodialysis system 100, a drain system 144 may be connected to the venous tubing 116 adjacent to the venous needle 118. The drain system 144 includes three clamps 134, 136 and 138 that are operated to open or close the tubing of the drain system 144. For example, when clamp 136 is opened clamp 134 is used to simultaneously clamp the line to the access site 128. Blood within the venous tube 116 now drains into a container in the outside environment and at atmospheric pressure, thereby simulating a venous needle 118 dislodgement without having to physically remove the needle from the access site 128. When the clamp 136 is closed and clamp 134 is opened, blood in the venous tube 116 is prevented from flowing through the drain system 144, and the blood flows through the needle and into the access site 128. In a similar manner, clamp 134 and clamp 138 are used to simulate a condition, partial dislodgment, where the venous needle is only partially dislodged form the access site and the needle remains under the tape used to secure the needle in place.

Figure 2:
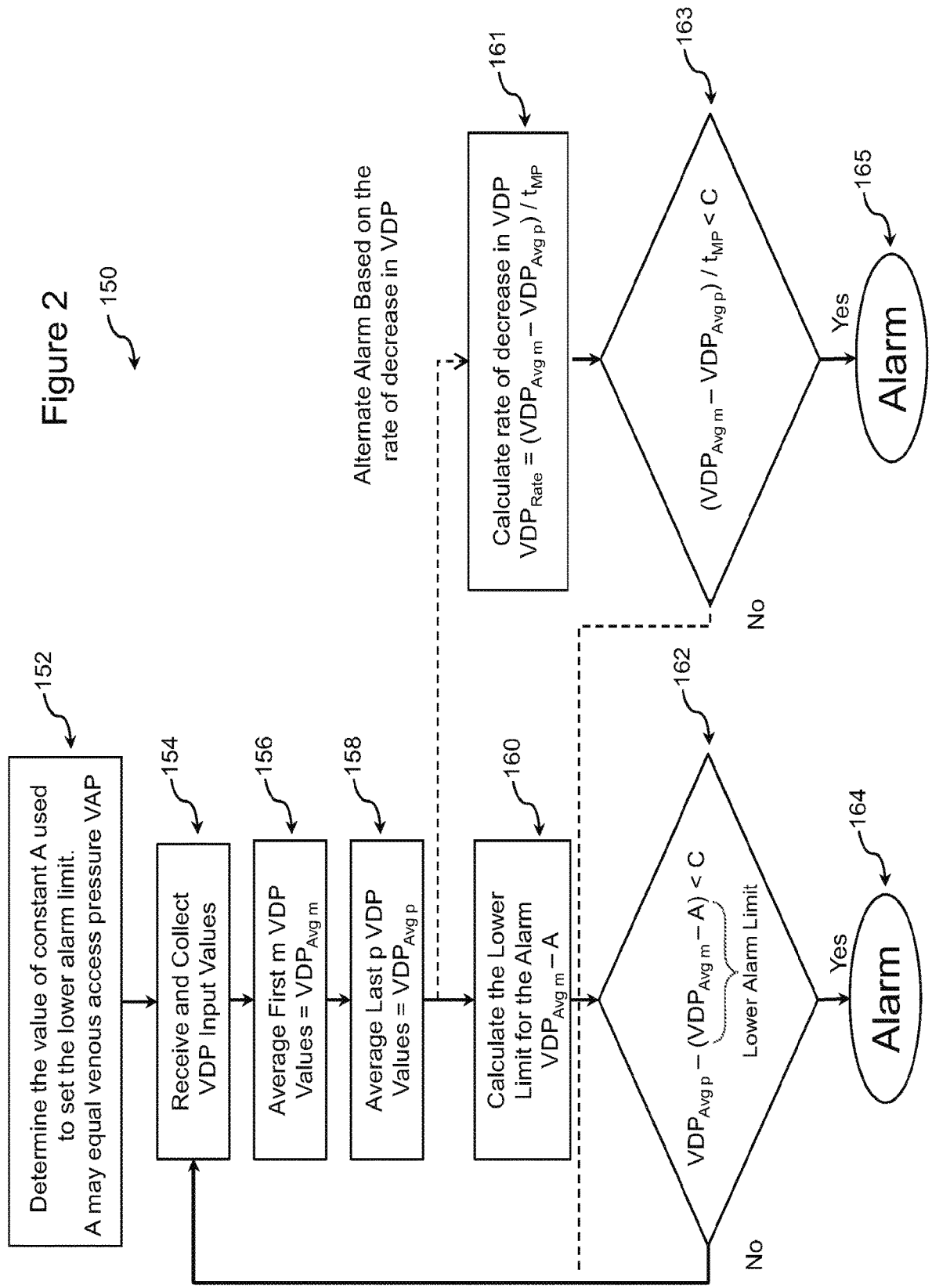
FIG. 2 is a flow chart illustrating a method for monitoring for needle dislodgement according to an embodiment.

FIG. 2 illustrates a flow chart of a method or algorithm 150 for monitoring for a needle dislodgement according to the present disclosure. The method 150 may have greater or fewer steps, and steps in the method may be rearranged, combined, or omitted in other examples. The method 150 may be implemented by the analyzer device and/or the detection device. In one example, the method 150 is implemented by a controller or computer in communication with the dialysis machine, such as machine 102.

The treatment is set up for a patient, or for the sham dialysis procedure. The reservoir 122 is filled, the access needles 104, 118 are inserted in to the access 128, and various parameters of the treatment, i.e. height, hematocrit, etc., are determined as needed.

At step 152, the value of the constant (A) used to set the lower alarm limit is determined and set. In one example, the venous access pressure is determined via measurement by stopping the pump 108 on the dialysis machine 102, for example, at the beginning of a treatment, such that the flow rate (Qb) is zero. The pressure indicated by the VDP sensor or transducer 114, corrected for the difference in pressure due to the height difference between the level of the VDP sensor 114 and the level of the access 128, is set as the access pressure. The controller 140 then sets the measured access pressure as the constant (A) for the treatment, and stores the constant in the memory unit 142. The constant (A) may be reset for each treatment for a patient, each time the machine 102 blood pump 108 is stopped such that the flow rate is zero, or if $VDP_0$ is recalculated during the treatment based on hematocrit. The constant (A) may vary across patients and across individual treatments. The measured access pressure, or constant (A), typically ranges between 5 to 80 mmHg.

The dialysis machine 102 blood pump 108 is then restarted such that blood is removed from the access 128 and arterial access needle 104, flows through the machine 102 and VDP chamber 112, and to the venous needle 118 and access 128.

At 154, the controller 140 receives a signal indicative of the VDP input pressure in real time from the sensor 114. The controller 140 may receive this signal at set time intervals based on the signal frequency. The signal frequency may be on the order of 1 cycle per second, or 1 Hertz, although faster signal frequencies are also contemplated since shortening the time to an alarm is desirable.

Figure 5:
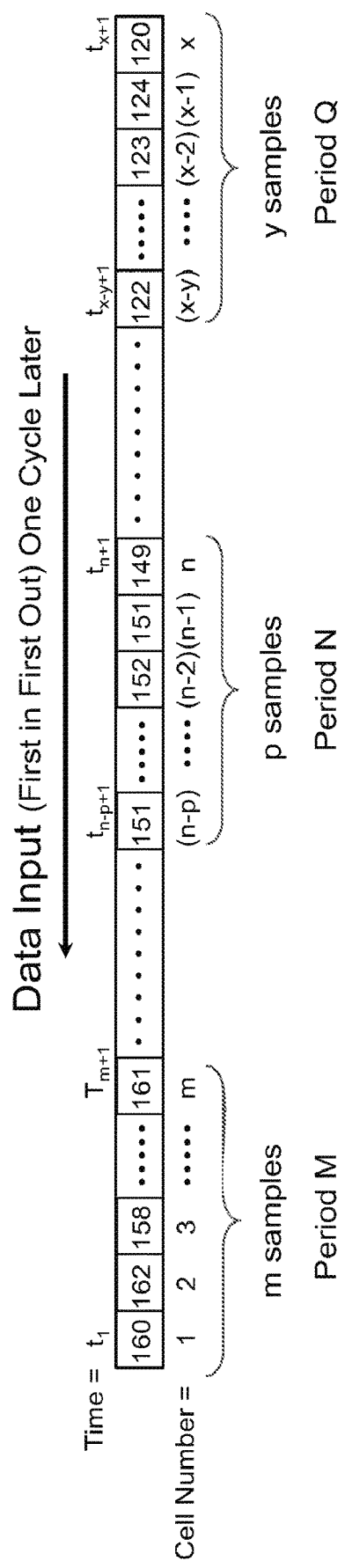
FIG. 5 is another matrix as used by the method as implemented by a controller at time (t+1) with multiple periods of data sampling.

The controller 140 collects the VDP values as they are received, and stores them in the memory unit 142, for example, into static random access memory (SRAM), flip-flops, latches or any other suitable form of storage. The controller 140 may use a matrix set as a row vector, fixed length queue, a shift register, or the like, to store the VDP pressures in a first-in-first-out (FIFO) strategy, or in the order that they were measured or received. An example of a matrix having (n) cells at a first time (t) for use by the controller 140 is illustrated in FIG. 3, and an example of the matrix at a second time one cycle subsequent to the first time is illustrated in FIG. 4. A further example of another matrix for use with the algorithm is illustrated in FIG. 5 and is used with multiple data sampling time periods.

In FIG. 3, the controller 140 has filled the (n) cells of the matrix 170 with the previous (n) VDP values received over times ($t_0$) to ($t_n$), with ($t_n$) being the most recent or present time. The VDP values are shown within the individual cells of the matrix 170, and are representative of VDP for a dialysis machine.

In FIG. 4, the matrix 170 is illustrated one cycle subsequent to FIG. 3 where the time has incremented by one cycle based on the signal frequency such that the present time is time ($t_{n+1}$). For example, with a signal frequency of 10 Hz, the time increment would be 0.1 seconds after the initial time, such that cell n of the matrix 170 is updated with the VDP value taken at time ($t_n$)+0.1 seconds. As can be seen from FIG. 4, the VDP values in the cells of the matrix 170 have shifted such that the value in cell 2 of the matrix in FIG. 3 is now the value of cell 1 in the matrix of FIG. 4, and the VDP value received at the present time ($t_{n+1}$) is stored in cell (n).

In one example, the controller 140 collects the previous twenty-five VDP measurements, such that n is 25. As the controller 140 continues to receive VDP measurements, the matrix is filled, and when the $26^{th}$ VDP value is reached and stored in the last cell (n) of the matrix, the VDP value in the first cell (1) is discarded as all of the values must shift. In other examples, the controller 140 may collect greater or fewer than the previous twenty-five VDP measurements such that n has another value. FIG. 3 shows that m samples are taken in sampling period M during time ($t_m$-$t_1$) and p samples are taken in sampling period P during time ($t_n$-$t_{n-p}$). The time ($t_{MP}$) between sampling periods M and P is ($t_{(n-p)}$-$t_m$).

At step 156 in FIG. 2, the controller 140 calculates the average or mean VDP value of the first (m) cells in the matrix 170 in FIG. 3 at a given or present time, e.g. ($t_n$) as $VDP_{Avg\ m}$. At step 158, the controller 140 calculates the average or mean VDP value of the last (p) cells in the matrix 170 at the same given or present time ($t_n$) as $VDP_{Avg\ p}$. The values of (m) and (p) may be set as a specified number of cells in the matrix 170. Note that in the present example, (m) is equal to (p); however, in other examples, the values of (m) and (p) may differ compared to one another, for example, with (p) being less than (m). Additionally, (m) and (p) may be set such that there is a block of cells in the matrix 170 that are positioned between the cells associated with the (m) and (p) blocks. By averaging the VDP values over a number of cells, the effects of system noise on the algorithm and method is reduced. The values of (m) and (p) may be set as a fraction of the total cells in the matrix 170. The values of (m) and (p) may be set as a value that minimizes the effects of noise while also minimizing the number of VDP values used in each average. In one non-limiting example, with the controller 140 collecting the previous 25 values, (m) and (p) are each set as five.

FIG. 3 additionally shows that m samples may be analyzed during time period M, and p samples are analyzed during time period P, with the time between periods M and P being $t_{MP}$=$t_{(n-p)}$-$t_m$ with (r) samples being collected during this time period. The sum of m, r, and p is equal to n in FIG. 3. The length of the time period $t_{MP}$ will contribute to the optimization of the analysis of the input data, in this case VDP.

FIG. 5 illustrates a variation on the method where multiple periods of data sampling may be stored, used and compared to determine a significant change in the input data, or VDP. During a decrease in VDP that occurs during dislodgment of the venous needle, VDP may drop by a pressure equivalent to the VAP in a short period of time, for example 10-15 seconds, or substantially similar to time period M to N. However, if the venous needle is only partially dislodged such that VDP decreases at a slower rate, an additional observation period may be needed, for example time period M to Q in FIG. 5. FIG. 5 therefore illustrates use of the method 150 to compare averaged VDP values taken at more than two time windows to detect a possible dislodgement event that occurs in either a short timeframe or more gradually.

Referring back to FIGS. 2-4, at step 160, the controller calculates the lower limit for the alarm based on average of the m samples taken during the time period M ($VDP_{Avg\ m}$) and the value for (A) that was set in step 152 using access pressure. The lower limit is set as: ($VDP_{Avg\ m}$-A).

At step 162, the controller compares the difference between the average of the p samples taken during time period P ($VDP_{Avg\ p}$) and the lower limit calculated in step 160 to a constant value (C) using the following equation:

$$VDP_{Avg\ p}-(VDP_{Avg\ m}-A)<C \qquad \text{Equation (3)}$$

The constant (C) may be set as a predetermined value. In one example, C is 0 mmHg. In another example, C is 3 mmHg, 5 mmHg, 10 mmHg, or another value. In another example, C is set as a function of the access pressure, or as a function of A, for example, as a predetermined percentage of A.

If $VDP_{Avg\ p}$-($VDP_{Avg\ m}$-A) is not less than the constant at step 162, the controller 140 returns to step 154 to receive and collect VDP values at time ($t_{n+2}$), such that the algorithm and method 150 continues to monitor for a needle dislodgement condition. The controller 140 may conduct steps 156, 159, and 160 for each new VDP value received into the matrix, or may conduct steps 156, 158, and 160 at specified intervals, for example, after receiving and collecting two or more new VDP values into the matrix 170.

If $VDP_{Avg\ p}$-($VDP_{Avg\ m}$-A) is less than the constant at step 162, the controller 140 proceeds to step 164 and sets an alert for a condition indicative of needle dislodgement. The controller 140 may send a communication or other alert to medical personnel, shut off the pump of the machine 102, and/or initiate other audible, visual, or vibratory alarms.

The method or algorithm 150 illustrated in FIG. 2 is not limited to the calculation of a simple lower limit shown in step 160 of the flow chart and a comparison to a fixed standard or constant as shown in step 162. The algorithm 150 may additionally or alternatively utilize any relevant mathematical calculation based on the calculation of $VDP_{Avg\_m}$, $VDP_{Avg\_p}$ and the time interval between them ($t_{MP}$) shown in FIG. 3. An alarm algorithm may utilize the rate of decrease in VDP during or across the time interval $t_{MP}$ compared to a standard as a method for activating an alarm, as shown as described with respect to steps 161, 163 and 165 in FIG. 3. It is also envisioned that the alarm algorithm may use multiple calculations with different sampling periods and time intervals. An alarm system that utilizes both the drop in VDP compared to a standard and the rate of the decrease in VDP compared to a standard has a shorter activation time for certain alarm situations. For example, if the venous access pressure is high, e.g. >60 mmHg, the rate of decrease in VDP needed to trigger an alarm may be calculated faster than the drop in VDP to the alarm limit. If venous access pressure is low, e.g. approximately 15 mmHg, the rate of decrease may not even trigger and alarm. It is also envisioned that the measured value of the venous access pressure may be utilized to optimize the alarm algorithm.

During treatment, the measured VDP may drift or change, for example, as the machine 102 warms up, as the hematocrit changes with changing total volume of blood in the patient causing a VDP rise, as infusing fluid into a patient during a hypotensive event decreases hematocrit causing a VDP decrease. The present method or algorithm 150 allows for this drift in the VDP. As the venous pressure measured by the machine (VDP) may drift up or down, the alarm limit set at step 160 by subtracting the access pressure from the mean of the first (m) VDP measurements or cells follows the up and down movements or drift of the venous pressure. Additionally, drift is generally insignificant when comparing $VDP_{Avg\_m}$ to $VDP_{Avg\_p}$ as the two values are calculated relatively closely to one another in time.

FIG. 6 illustrates a diagram representing the VDP averages as discussed with respect to FIGS. 2 and 3. FIG. 6 plots venous pressure, or VDP, as measured by the machine 102 versus time. Windows indicating average VDP values are indicated on the Figure, with those associated with $VDP_{Avg\_m}$ labeled as an (m) window, and those associated with $VDP_{Avg\_p}$ labeled as a (p) window. A needle dislodgement occurs at time $t_d$ between times $t_m$ and $t_{n-p}$ such that the VDP begins to drop. As such, the following $VDP_{Avg\_p}$ value is lower than the $VDP_{Avg\_m}$ value just following $t_d$, and the controller 140 would proceed to activate 164 and set the alert.

The method 150 or algorithm is directed to monitoring for a change in a VDP as indicated by comparing the present average VDP to a recent average VDP, opposed to monitoring for a value of VDP or calculated VAP. As such, the controller 140 is able to determine a condition indicative of a needle dislodgement sooner. Testing using the sham dialysis system as illustrated in FIG. 1 indicated that the present monitoring algorithm 150 is able to detect a needle 118 dislodgement in advance of conventional dialysis machine 102 alarm being set off, and was also able to detect a needle 118 dislodgement when the conventional alarm in the machine 102 was not set off at all.

During a dialysis procedure, an adverse event may occur if the dialysis machine is simply reset without an operator observing that the venous needle 118 has been completely dislodged or partially dislodged. If the machine is reset, it will resume operation based on the assumption that it is operating with a valid or safe set of operational parameters including a safe venous drip chamber pressure, when in fact the needle 118 is at least partially dislodged. To avoid this situation, the method 150 may read the venous access pressure when the alarm system has already stopped the dialysis machine blood pump 108, for example, using the procedure based on step 152. If the venous access pressure has not returned to a normal level or is determined to be within an acceptable pressure range, the method 150 may act to prevent an operator reset of the machine and the resumption of operation, or act to provide an additional warning or alert to the operator when the operator attempts to reset the machine.

FIG. 7 illustrates a flow chart of another method or algorithm 180 for monitoring for a needle dislodgement according to the present disclosure. The method 180 may have greater or fewer steps, and steps in the method may be rearranged, combined, or omitted in other examples. The method 180 may be implemented by the analyzer device and/or the detection device. In one example, the method 180 is implemented by a controller or computer in communication with the dialysis machine, such as machine 102. The method 180 is implemented in a similar manner as that described above with respect to method 150.

At step 182, the value of the constant (A) used to set the lower alarm limit is determined and set. In one example, the venous access pressure is determined as a static access pressure. The controller 140 sets the measured access pressure as the constant (A) for the treatment, and stores the constant in the memory unit 142. The constant (A) may be reset for each treatment for a patient, each time the machine 102 pump 108 is stopped such that the flow rate is zero, or if $VDP_0$ is recalculated during the treatment based on hematocrit. The constant (A) may vary across patients and across individual treatments. The measured access pressure, or constant (A), typically ranges between 5 to 80 mmHg.

The dialysis machine 102 pump 108 is then restarted such that blood is removed from the access 128 and arterial access needle 104, flows through the machine 102 and VDP chamber 112, and to the venous needle 118 and access 128.

At step 184, the controller 140 receives a signal indicative of the VDP input pressure in real time from the sensor 114. The controller 140 may receive this signal at set time intervals based on the signal frequency. The signal frequency may be on the order of 1 cycle per second, or 1 Hertz, although faster signal frequencies are also contemplated since shortening the time to an alarm is desirable.

At step 186, the controller 140 calculates an average or mean VDP, and corrects the VDP for height and/or drift, as described in further detail below. The mean corrected VDP may be based on an average of a recent history of VDP measurements, for example, as a running average, using the most recent five, ten, or another number of VDP inputs in the average.

At step 188, the controller 140 calculates the lower limit for the alarm using the standard curve ($VDP_S$) and the value for (A). The lower limit is set as: ($VDP_S - A$).

At step 190, the controller compares the difference between the mean corrected VDP and the lower limit calculated in step 188 to a constant value (C) using the following equation:

$$VDP_{Avg\_Corr} - (VDP_S - A) < C \qquad \text{Equation (4)}$$

The constant (C) may be set as a predetermined value, and may be the same value as is used above with reference to method 150. In one example, C is 0 mmHg. In another example, C is 3 mmHg, 5 mmHg, 10 mmHg, or another value. In another example, C is set as a function of the access pressure, or as a function of A, for example, as a predetermined percentage of A.

If $VDP_{Avg\_Corr}-(VDP_S-A)$ is not less than the constant at step 190, the controller 140 returns to step 184, such that the algorithm and method 180 continues to monitor for a needle dislodgement condition.

If $VDP_{Avg\_Corr}-(VDP_S-A)$ is less than the constant at step 190, the controller 140 proceeds to step 192 and sets an alert for a condition indicative of needle dislodgement. The controller 140 may send a communication or other alert to medical personnel, shut off the pump of the machine 102, and/or initiate other audible, visual, or vibratory alarms.

Method 180 and various embodiments according to the present disclosure are further described in detail by reference to the following experimental examples. These examples are provided for the purpose of illustration only, and are not intended to be limiting unless otherwise specified. Thus, the invention should in no way be construed as being limited to the following examples, but rather, should be construed to encompass any and all variations that become evident as a result of the teaching provided herein.

Figure 8A:
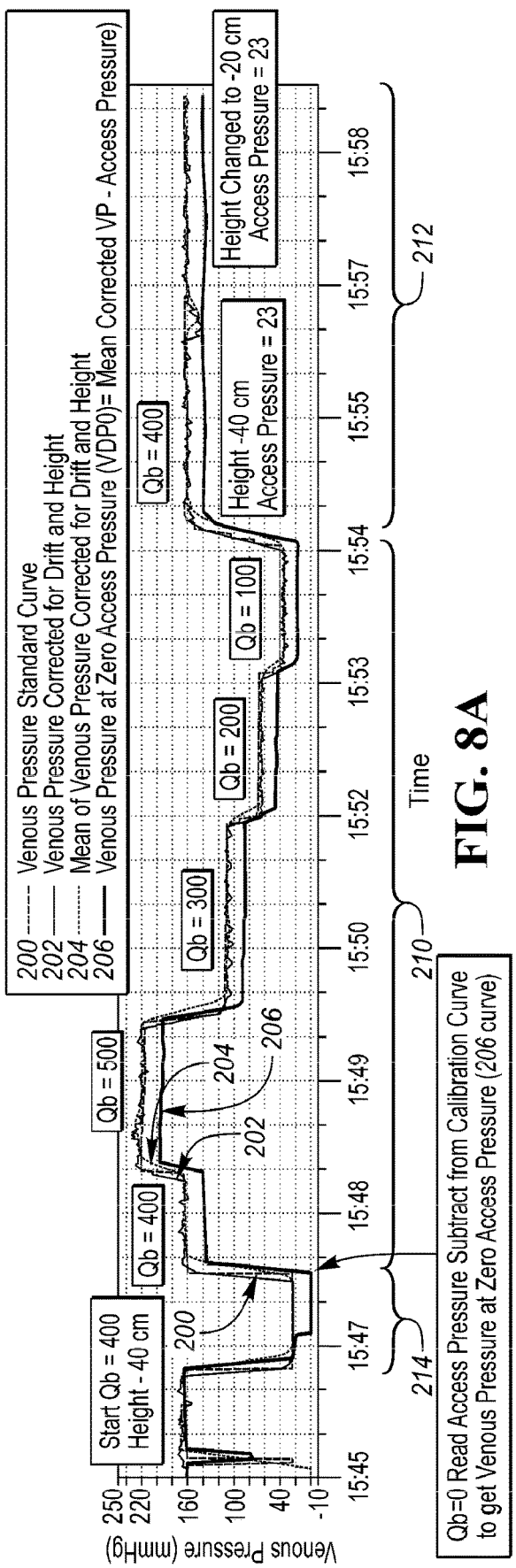
FIGS. 8A and 8B plot various pressures and values with respect to time as measured by the system or calculated by the controller during a sham dialysis procedure.
Figure 8B:
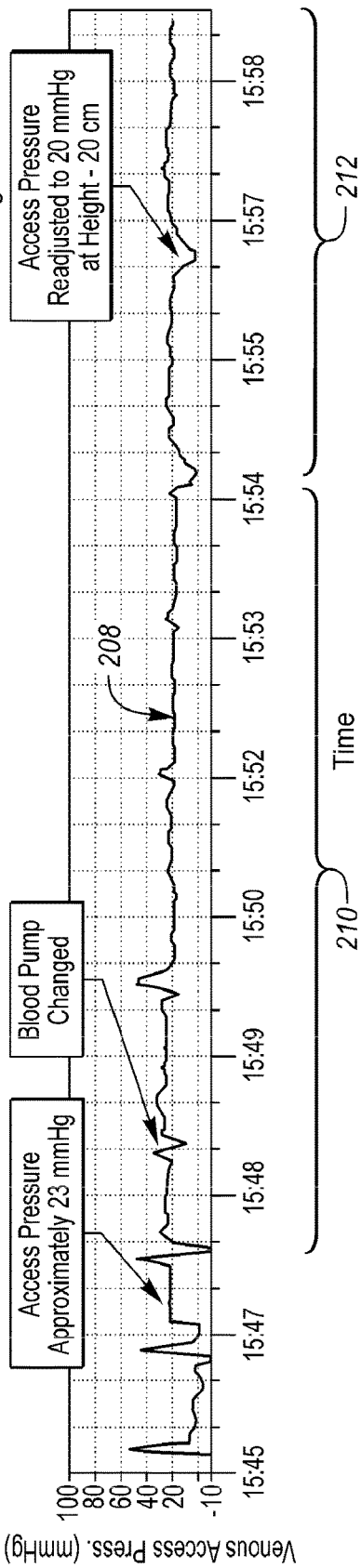

FIGS. 8A and 8B plots various measured and calculated pressures and values with respect to time that the controller 140 uses to monitor venous access pressure for venous needle dislodgment. The pressures and values as shown in FIGS. 8A-8B may additionally be used as part of a calibration process, as the pump 108 transitions across a range of flow rates. FIGS. 8A and 8B are linked such that they illustrate the same time window.

In FIG. 8A line 200 represents the standard curve for VDP ($VDP_S$). $VDP_S$ may be determined by various methods to establish a fixed value of VDP at any blood flow rate. This standard curve may be used to correct the raw input data for drift. Since the raw input data is not corrected for height, the drift correction factor may be obtained by subtracting the $VDP_S$ value minus the height correction factor in mmHg from the raw input value of VDP read at sensor 114. The corrected VDP is illustrated as line 202 and is determined by correcting raw VDP for the height or distance between the VDP chamber 112 and the access 128 and also correcting VDP for the drift in pressure in VDP measured at sensor 114. The method of determining a corrected VDP 202 is described in further detail below with respect to FIGS. 9-10. The averaged corrected VDP is illustrated by line 204 and represents a mean or averaged value of corrected VDP 202, in this case a 10-second moving average, and corresponds to the value calculated in step 186 of method 180. Line 206 represents $VDP_0$ as calculated in equation (2), or as calculated as the mean corrected VDP 204 minus a current measurement of the venous access pressure, and is the venous pressure alarm limit for venous needle dislodgment, as described above in step 188. FIG. 8B shows the measured access pressure as line 208.

FIGS. 8A-8B illustrate the changes in pressures that occur with changing flow rates of the pump 108 and changing access site heights ΔH. In FIGS. 8A-8B, the data displayed in time window 210 shows that the controller 140 may adjust all measurement parameters and alarm conditions across a range of different blood flow rates (Qb). In FIG. 8B the access pressure 208 remains stable across the range of blood flow rates with only transient changes immediately following a change in the blood flow rate. In region 212 of FIG. 8A, the data shows that venous pressures 202, 204 and the alarm limit 206 are stable when access height is initially 40 cm below the height of the venous pressure sensor 114 measurement site with blood flow held constant at 400 ml/min. Venous pressures 202, 204 and the alarm limit 206 remain stable in region 212 when the access height is reduced to 20 cm below the height of the venous pressure sensor 114 measurement site. In region 212 of FIG. 8B, the venous access pressure 208 remains at approximately 20 mmHg except for a transient response when the height is changed from 40 cm to 20 cm below the height of the venous pressure sensor 114 measurement site.

Figure 9:
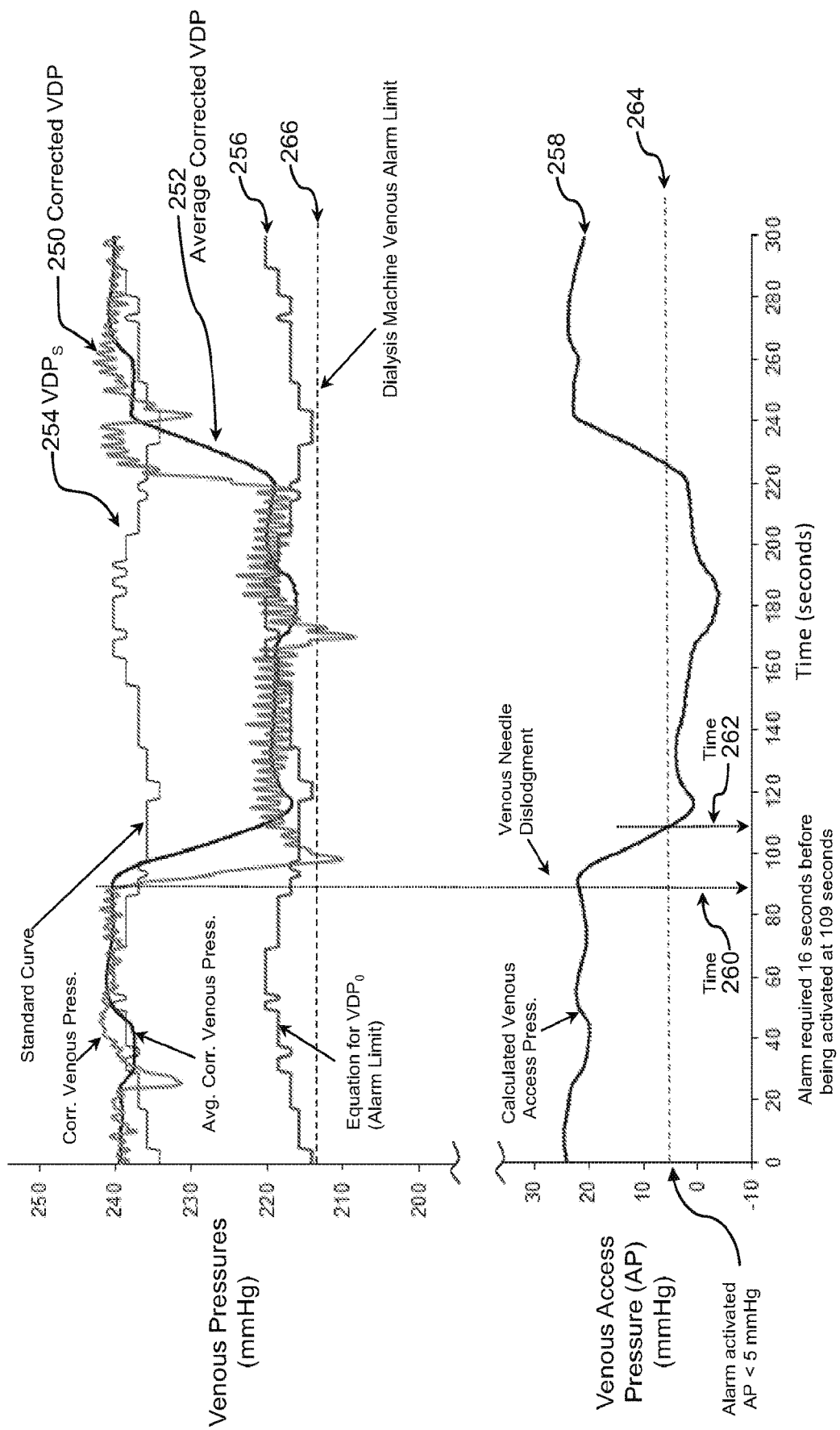
FIG. 9 plots various pressures with time as measured by the system or calculated by the controller during a sham dialysis procedure mimicking a calibration process and a venous needle dislodgement from an access pressure of 20 mmHg using the method as illustrated in FIG. 7.

FIG. 9 plots various pressures as measured or calculated by the controller 140 as part of a calibration process, which may include step 182 of determining access pressure. Line 250 represents a corrected VDP, such as that described above with respect to line 202 in FIG. 8B, where the corrected VDP is corrected for height and drift. Line 252 represents the mean or averaged value of corrected VDP 250, in this case a 10-second moving average, such as that described above with respect to line 204 in FIG. 8A and step 186 in method 180.

In FIG. 9, line 254 represents the standard curve for VDP, such as that described above with respect to line 200 in FIG. 8A. It should be noted that the measured value of the raw input VDP data is always due in part to the patient's venous access pressure. The corrected venous pressure line 250 is the raw input VDP corrected for height and corrected for drift using the drift correction factor. It should be noted that the drift correction factor is calculated for both increases and decreases in the raw input VDP. Drift correction factor values may be stored in memory locations, for example, in a matrix, and a running average of the drift correction factor may be calculated and used.

Figure 10:
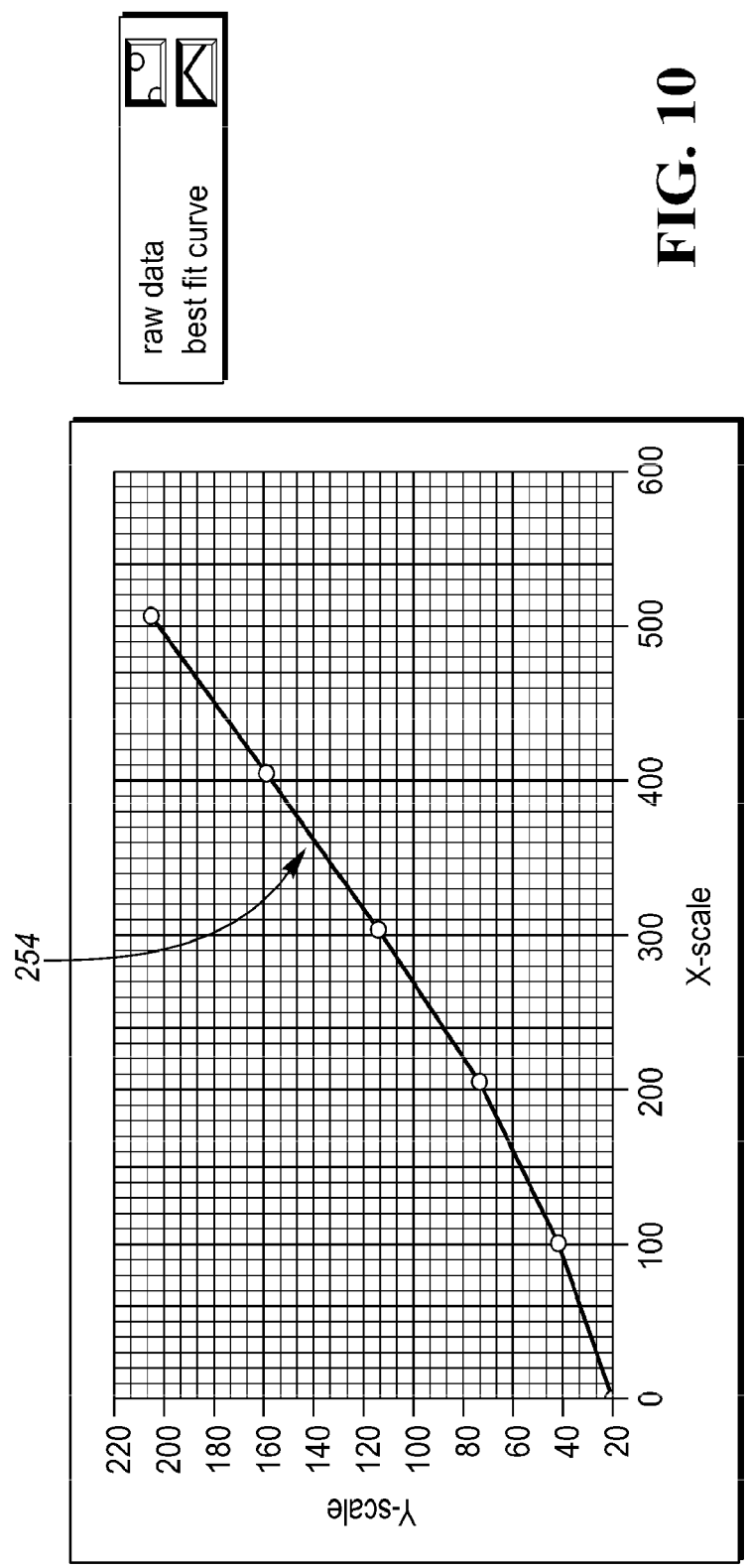
FIG. 10 plots a standard curve.

The standard curve $VDP_S$ 254 may be calculated for each individual patient by using the controller 140 to set the dialysis machine blood pump 108 to different blood flow rates, for example, as shown in region 210 of FIG. 8A, and recording an average of the raw VDP for each blood flow rate corrected for height and then fitting a mathematical formula to the data. FIG. 10 shows the results of a method or algorithm that may be embedded into controller 140 to calculate a standard curve 254 for a sham dialysis experiment. The standard curve 254 may be used to continuously calculate a $VDP_S$ value because the blood pump continuously reports its current blood flow rate to the dialysis machine computer and the controller 140. The standard curve 254 calculated using this method has the advantage that it is using the current patient's blood in the extracorporeal circuit therefore any correction for the patient's hematocrit is not needed. Using this method, the standard curve 254 may additionally be corrected for changes in the patient's hematocrit if a device is placed in the extracorporeal fluid circuit to constantly monitor hematocrit. The standard curve 254 may also be the value of the venous access pressure added to the $VDP_0$ calculated in equation (2), where the venous access pressure may be determined via step 152 in region 214 of FIG. 8A. The standard curve 254 may also be any value of VDP that is related to the machine blood pump blood flow rate. An example of this is an average VDP value calculated for a number of patients at varying blood flow rates. By setting the alarm limit for venous needle dislodgment equal to the standard curve minus the access pressure as shown in step 188, the determination of an alarm condition is not affected by drift in the raw input value of VDP as measured by the sensor 114.

Referring back to FIG. 9, line 256 is equivalent to $VDP_0$ as calculated in equation (2), or line 256 may alternatively be calculated as the standard curve 254 minus the current measurement of the venous access pressure as determined at step 182, and is the venous pressure alarm limit for venous needle dislodgment. FIG. 9 plots the mean access pressure as line 258, where the access pressure is measured using the mean VDP line 252 minus the mean $VDP_0$ value line 256.

FIG. 9 illustrates a venous needle dislodgment event starting at time 260. Since the corrected venous pressure line 250 is corrected for both upward and downward drift in the raw VDP input data obtained at sensor 114, a drop in VDP associated with venous needle dislodgment needs to be distinguished from a downward drift of the raw input data, as both may cause a decrease in the corrected VDP 250. Normally, physiological changes will not cause rapid changes in the raw value of VDP, therefore a memory storage system 142 and a matrix may be used to monitor the raw input VDP data 200 for a sharp drop in the incoming VDP values measured at sensor 114.

In one example, a method or algorithm 150, 180 similar to the one described with respect to FIGS. 2 and 7 may determine that there is a significant drop in the raw VDP values within a prescribed time interval, for example 15 mmHg in less than 15 seconds. The algorithm then stops the use of the current venous correction factor and implements the use of a mean correction factor that was recorded previously and stored, for example recorded 15 seconds in the past. Using the venous pressure correction factor from 15 seconds in the past allows the corrected venous pressure line 250 and the average corrected venous pressure line 252 to drop in response to the rapid drop in the raw VDP values. When the average corrected venous pressure 252 drops to within a set value, for example 5 mmHg, above $VDP_0$ 256, the venous needle dislodgment alarm is activated at time 262. The alarm limit is also shown with respect to access pressure 258 as line 264. The mean correction factor that was recorded 15 second in the past may be reset after dialysis staff investigates and addresses the venous needle alarm or it can be used for any length of time after the machine is reset to determine if the access pressure has returned to an acceptable level, which may require the correction factor to be adjusted or scaled if a different blood flow is used after resetting the alarm. The dialysis machine venous pressure alarm limits may be automatically adjusted at the start of the experiment or procedure to the upper and lower limits. The upper dialysis machine venous pressure alarm limit is set as the current raw VDP value plus a predetermined value, e.g. 80 mmHg, such that the upper limit is 318 mmHg in FIG. 9. The lower dialysis machine venous pressure alarm limit is set as the current raw VDP value 200 minus 25 mmHg, and is shown as line 266 at 213 mmHg in FIG. 9. Note that in the present example, the average corrected VDP 252 never reached the dialysis machine lower alarm limit 266 when the needle was dislodged after the event at time 260, such that the conventional machine alarm was not activated by the machine even though the corrected VDP line 250 dropped below the machine alarm limit line 266, indicating that the dialysis machine is also comparing an average VDP to the alarm limit 266.

Figure 11:
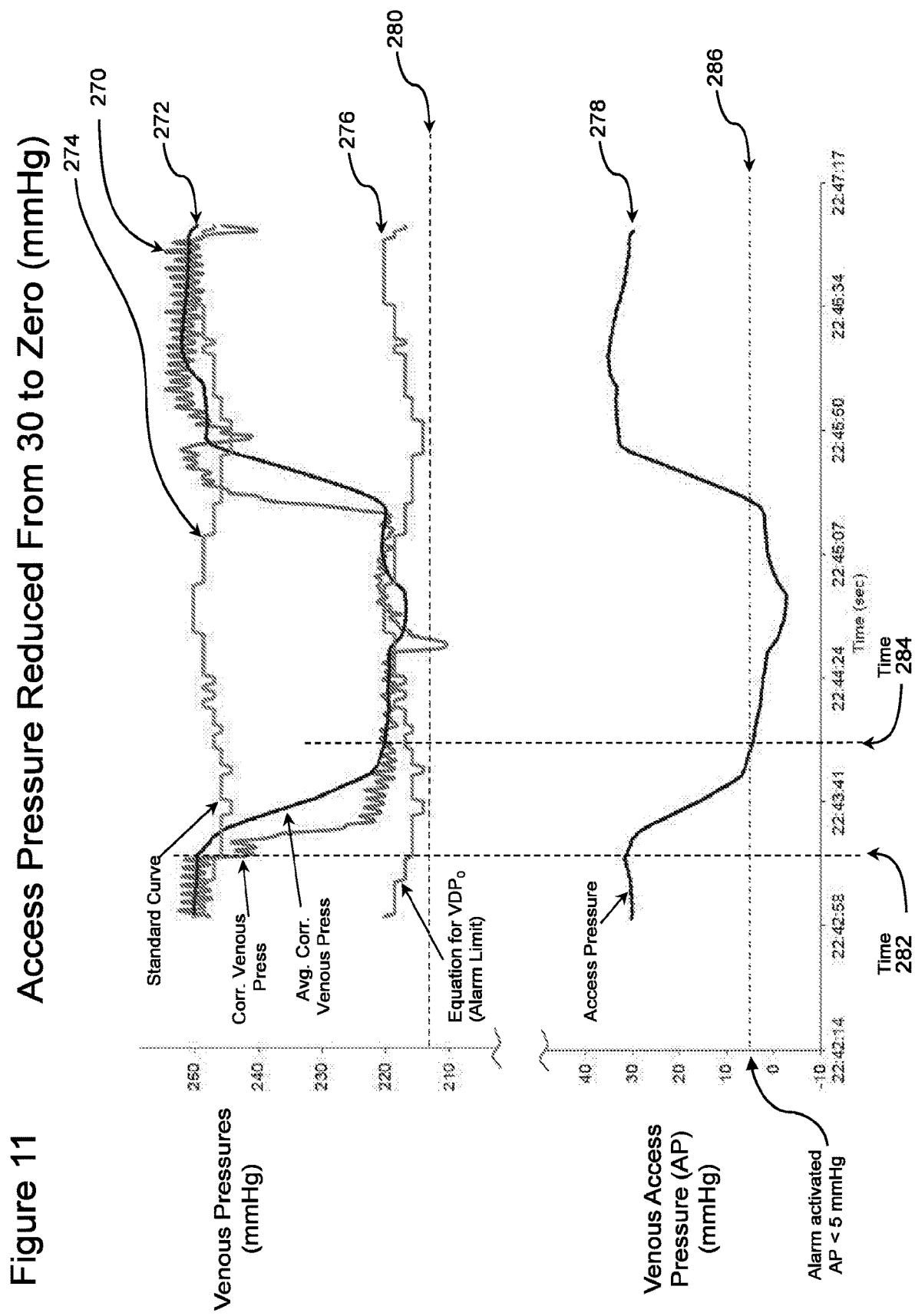
FIG. 11 plots various pressures with time as measured by the system or calculated by the controller during a sham dialysis procedure mimicking a venous needle dislodgement from an access pressure of 30 mmHg.

FIG. 11 illustrates experimental results of simulated venous needle dislodgment when the starting access pressure is set at 30 mmHg and implementing the method 180. In FIG. 11 the corrected venous pressure is line 270, average corrected venous pressure is line 272, the standard curve is line 274, and the alarm limit based on venous pressure with zero access pressure is line 276. FIG. 11 also shows the drop in the access pressure line 278 in response to a needle dislodgment event or in response to lowering the blood reservoir 122 to decrease access pressure to zero to simulate a venous needle dislodgement and activating the venous needle dislodgment alarm. The experimental data in FIG. 11 was recorded shortly after the data was recorded for FIG. 9. To record this data, the reservoir 122 was raised to increase the access pressure from 20 mmHg to 30 mmHg, which increased the raw VDP values by 10 mmHg, which is equivalent to an upward drift of 10 mmHg in the raw VDP pressure measured at sensor 114. The alarm limits for the dialysis machine were fixed at 318 mmHg and 213 mmHg as described above with respect to FIG. 9, and were not adjusted when the raw VDP values increased by 10 mmHg to approximately 248 mmHg, which is normal practice for the majority of conventional dialysis machines in use today. The lower machine alarm limit 280 is now 35 mmHg below the level of the current VDP pressure value of 248 mmHg. Under these conditions, the venous pressure recorded by the dialysis machine would have to drop 35 mmHg before the machine venous pressure alarm would be activated. FIG. 11 does show a point where corrected venous pressure 270 drops below the machine venous pressure lower alarm limit 280, however line 270 does not directly represent the average venous pressure data used by the dialysis machine to compare to the alarm condition 280. As shown in FIG. 11, after the simulated needle dislodgement event at time 282, the venous needle dislodgment alarm is activated at time 284 when the average corrected venous pressure 272 drops to within a set value, for example 5 mmHg, above $VDP_0$ 276. The alarm limit is also shown with respect to access pressure 278 as line 286. The experimental data in FIG. 11 show that the conventional dialysis machine venous pressure alarm was not activated after a dislodgement event at time 282 because if the conventional machine alarm had activated, the Figure would show all venous pressure readings dropping toward zero in response to the conventional machine venous pressure alarm stopping the blood pump.

Figure 12:
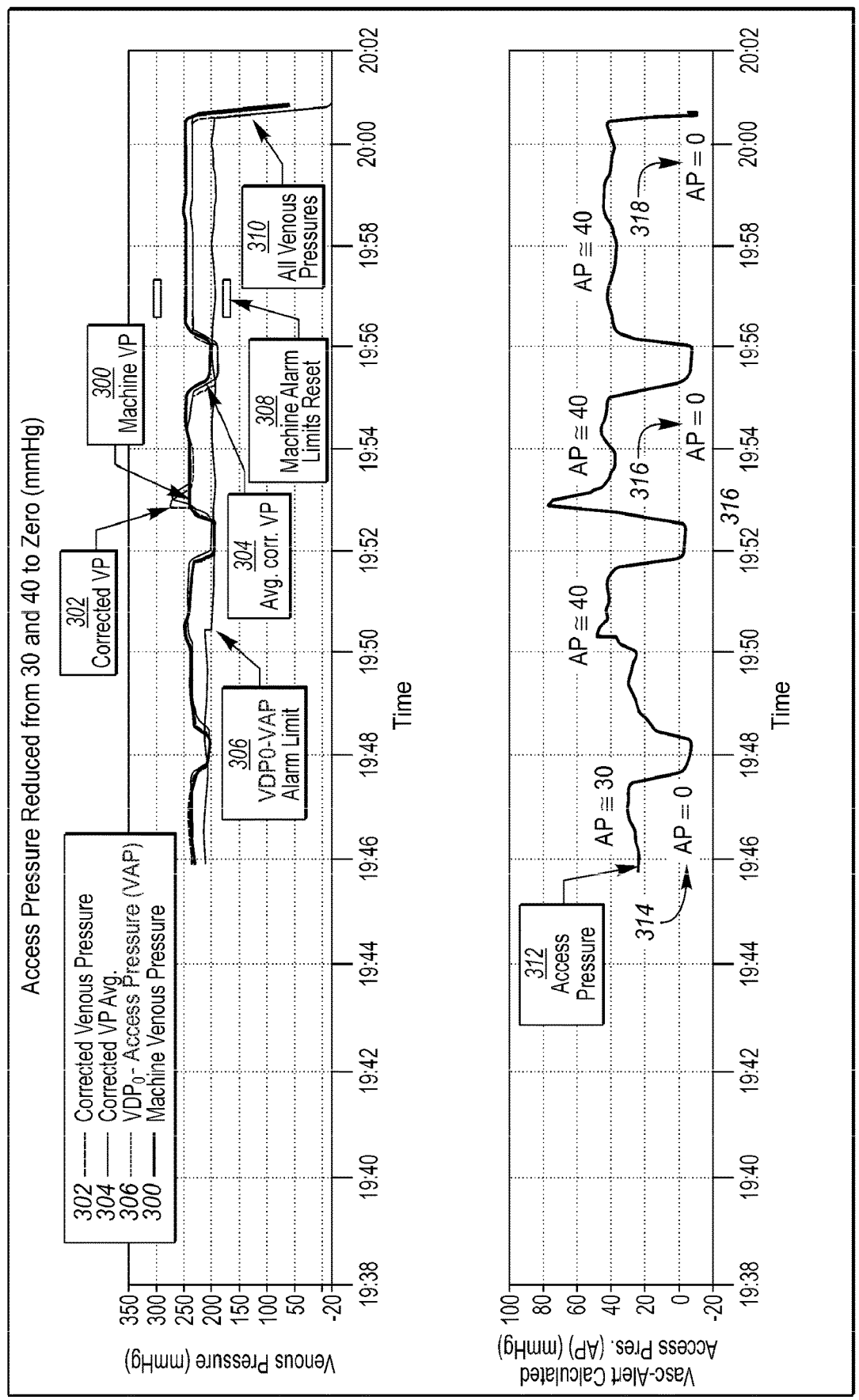
FIG. 12 plots various pressures with time as measured by the system or calculated by the controller and illustrates a conventional machine alarm under the influence of changes in access pressure and/or drift.

FIG. 12 illustrates raw machine venous pressure 300 recorded at sensor 114, corrected venous pressure 302, average corrected venous pressure 304 and the venous access pressure alarm limit 306 as well as the access pressure 312 in the lower portion of the graph. The data presented in FIG. 12 is very similar to the data presented in FIG. 11. The initial access pressure was 20 mmHg and increased to 30 mm Hg, representing an upward drift of 10 mmHg and resulting in a conventional machine alarm lower limit that is 35 mmHg below the current machine venous pressure 300 (opposed to the original 25 mmHg below the venous pressure). When access pressure 312 was reduced from 30 mmHg to zero at event 314, the conventional machine venous alarm was not activated. Access pressure was increased to 40 mmHg and the conventional machine venous alarm lower limit was now 45 mmHg below the current venous pressure 300. When the access pressure 312 was reduced to zero there was again no activation of the conventional machine venous alarm. The conventional machine venous alarm limits 308 were reset after event 316 so that the conventional machine venous alarm lower limit was 25 mmHg below the current venous pressure 300. When access pressure 312 was reduced to zero at event 318, the conventional machine alarm was activated and the blood pump stopped. When the conventional machine venous pressure alarm was activated by dropping the access pressure 312 to zero all measured or calculated venous pressures at 310 dropped toward zero because the blood pump had stopped and the raw venous pressure 300 became zero.

Figure 13:
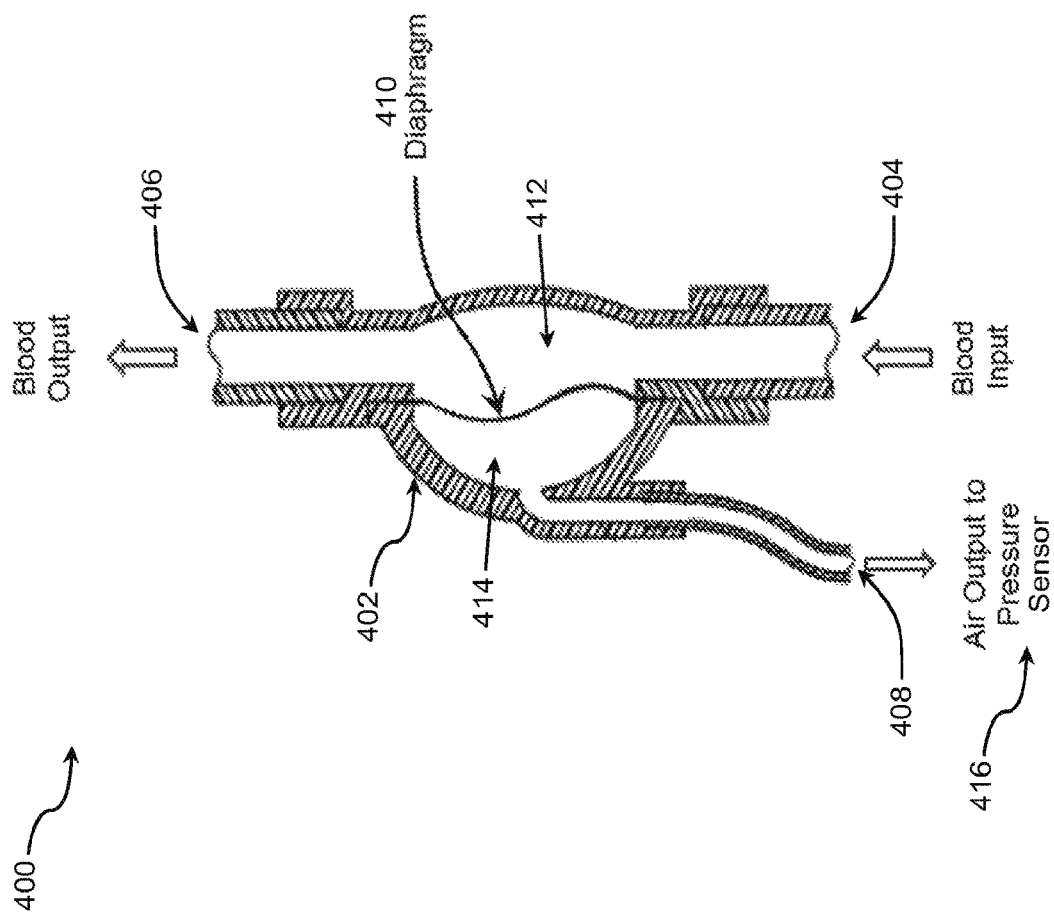
FIG. 13 illustrates a pressure measurement device with two chambers separated by a diaphragm for use with the dialysis machine of FIG. 1 according to an embodiment, where pressure is transferred from a chamber containing fluid to a chamber containing air.

In another example, Equation (2) may be used in a further safety application for pressure monitoring circuits that have a device that incorporates a diaphragm in a pressure chamber to transfer fluid pressure to air pressure that is then read by a pressure sensor. FIG. 13 illustrates a schematic of a device 400 that incorporates a pressure measurement pod 402 with a diaphragm 410 for use with medical fluids. The device 400 may be incorporated into a dialysis machine, such as dialysis machine 102, for pressure sensing. The device 400 has a housing 402 or pressure pod 402 that defines two chambers 412, 414 separated by a flexible diaphragm 410. Blood in the extracorporeal circuit tubing flows into the blood input 404 then passes into the first fluid chamber 412 of the device where pressure in the blood is transferred across the diaphragm 410 to the second fluid chamber 414 by movement of the diaphragm 410. The second chamber 414 may contain air or another fluid. Blood then flows out of the chamber 412 through the blood output 406 back into the extracorporeal tubing. The pressure transferred from the blood across the diaphragm 410 to the air chamber 414 is then measured by a pressure sensor 416. The device 400 provides a method of measuring the pressure of the blood without the need for a blood-air interface. The pressure monitoring device 400 may additionally reduce heparin needs and clotting in the extracorporeal circuit.

Systems using a diaphragm 410 to transfer pressure from one pressure compartment 412 to another pressure compartment 414 require the diaphragm to have enough room to move or travel within the housing 402 such that pressure may be accurately and precisely recorded over a desired pressure range. The device 400 may have an incorrect pressure measurement if the diaphragm becomes misaligned or mispositioned within the housing 402. For medical devices using the device 400, this may cause a safety concern when the diaphragm 410 is moved out of the correct position, as an incorrect pressure will be sensed by the device 400.

Figure 14:
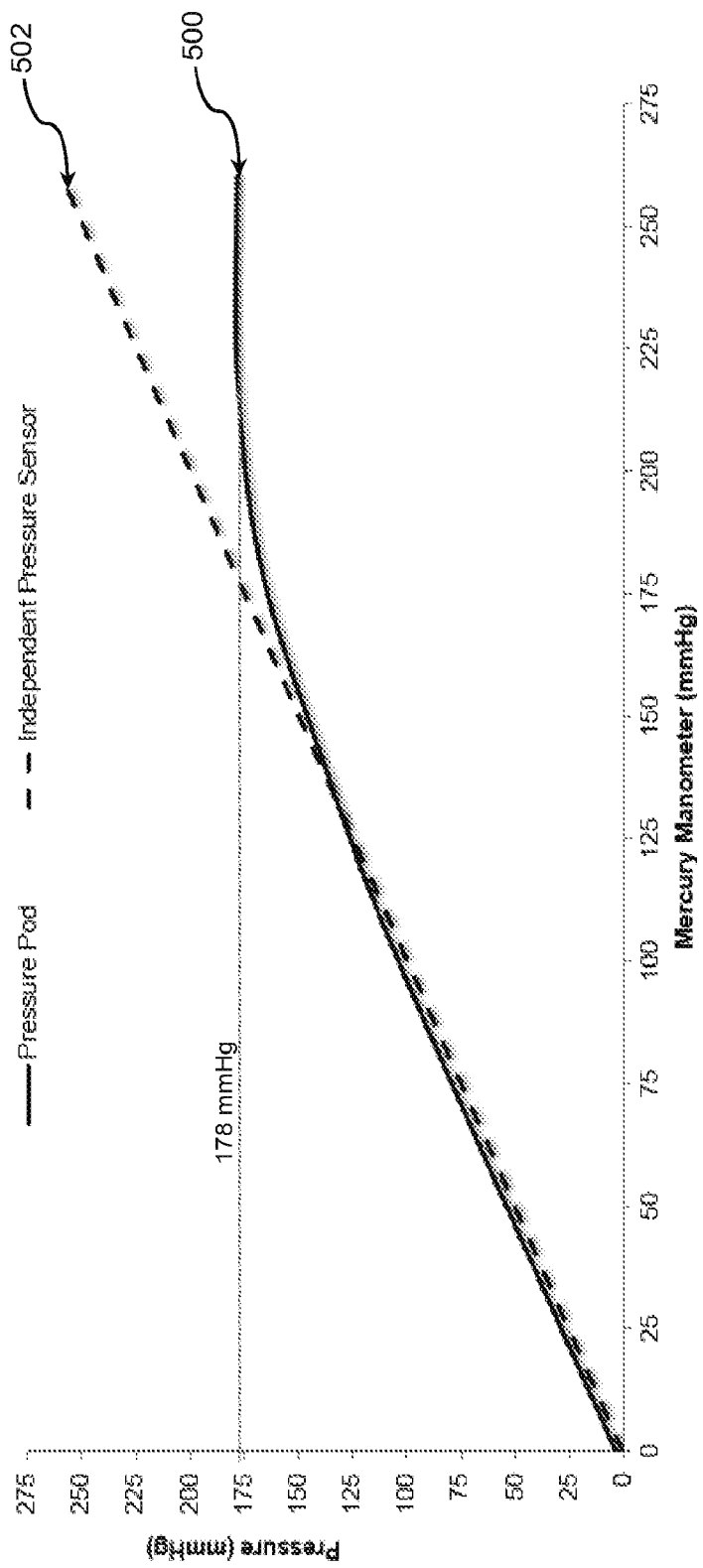
FIG. 14 plots pressure measured by the device of FIG. 13 at the air output line with the diaphragm out of position and pressure measured by an independent pressure transducer connected to the blood output across a pressure range from 0 to 260 mmHg.

FIG. 14 is a graph illustrating measured pressure (mmHg) versus pressure as recorded by a mercury manometer (mmHg). Line 500 illustrates the pressure as measured by the device 400 across a range of blood pressures, and line 502 illustrates the pressure as measured by the independent pressure sensor adjacent to the device. As can be seen in the Figure, line 500 deviates from the actual pressure at higher pressure values, and this may be caused by the diaphragm 410 reaching a limit such that there is no longer any more air to compress in the air chamber 414 or the travel of the diaphragm is limited. In the present example, the pressure sensor 416 cannot read any pressures higher than approximately 178 mmHg as shown by line 500, while the independent pressure sensor as shown by line 502 continues to accurately and precisely read the increase in pressure created by the mercury manometer.

FIG. 15 illustrates the results of testing the device 400 in a sham dialysis circuit with the membrane 410 out of position and in the correct position. Blood is introduced into the chamber 412 and the pressure is recorded by the pressure sensor 416. An independent pressure sensor is placed in the extracorporeal circuit downstream of the blood output 406 but at the same level as the pressure pod to avoid any pressure error between the two sensors due to a difference in height of the measurement locations. The device 400 is illustrated at 600 as having the diaphragm 410 out of position with blood flow (Qb) in the sham dialysis circuit at 250 ml/min, and pod venous pressure at ≅95 mmHg and independently measured at ≅92 mmHg. The device 400 is illustrated at 602 as having the diaphragm 410 out of position with blood flow (Qb) at 500 ml/min, and pod venous pressure at ≅158 mmHg and independently measured as ≅224 mmHg. The device 400 is illustrated at 604 as having the diaphragm 410 in position such that the device is operating in a design condition with blood flow (Qb) at 500 ml/min, and pod venous pressure at ≅234 mmHg, and independently measured at ≅227 mmHg.

FIG. 16 illustrates the results of sham dialysis testing of the venous pressure pod device 400. Venous pressure measurements were made with the dialysis machine pressure pod 400 and an independent venous pressure transduce measurement placed in the extracorporeal circuit adjacent to the device 400, for example, downstream of the blood output 406. The device 400 pressure measurement is illustrated as line 704, and the independent pressure transducer measurement is illustrated as line 714.

The pressure pod diaphragm 410 was placed out of position at the start of sham dialysis, in the configuration as shown at 600 in FIG. 15. The dialysis machine blood flow rate was set to 250 ml/min at 718, and pressure pod sensor 416 and the independent sensor both read approximately 92 to 95 mmHg, as shown by arrow 718. When machine blood flow was increased to 500 ml/min as shown by arrow 720 corresponding to configuration 602 in FIG. 15, the pressure pod measurement 704 increases to only 158 mmHg while the independent sensor reading 714 increases to approximately 224 mmHg, corresponding with the true pressure in the circuit. To demonstrate measurement inaccuracies in the device 400 and a possible associated safety risk with the use of the pressure pod 400 measurements, venous needle dislodgment was simulated by simultaneously closing clamp 134 and opening clamp 136, and is shown at 710 in FIG. 16. Under these conditions, the independent venous pressure sensor measurement 714 dropped approximately to the venous pod sensor measurement 704 of approximately 150 mmHg and the dialysis machine did not generate a venous pressure alarm and did not stop the dialysis machine blood pump which would have otherwise caused pressures 704 and 714 to drop to zero. The circuit was then restored to the conditions prior to simulated venous needle dislodgment 710 by closing clamp 136 and opening clamp 134.

In order to test a simulated venous needle dislodgment with the pressure pod diaphragm in the correct position, the blood pump was stopped at 722, the pressure pod diaphragm reset to correct position and machine blood flow reset to 500 ml/min such that the device 400 is in the configuration as shown at 604 in FIG. 15. With the venous pod diaphragm 410 in the correct position, the venous pod sensor 416 had a pressure reading 704 of approximately 234 mmHg as shown at 708. Under these conditions, a venous needle dislodgement was simulated at 712 by closing clamp 134 and opening clamp 136, and the venous pod 400 sensor 416 accurately measured venous pressure. Immediately after simulated venous needle dislodgment at 712, the dialysis machine blood pump was stopped by the alert and all recorded pressures therefore dropped to zero.

Equation (2) is used to calculate $VDP_0$ and is the dialysis machine venous pressure when the venous access pressure is equal to zero. When venous access pressure (VAP) is added to $VDP_0$, the result is an accurate estimate of the current venous pressure that should be measured or recorded by the dialysis machine venous pressure pod 400 sensor 416, as shown by Equation (1). $VDP_0$ added to VAP is also equivalent to the standard curve 254 as calculated and described with respect to FIG. 10. The standard curve 254 is plotted as line 706 in FIG. 16, and FIG. 16 illustrates how the standard curve 706 may be utilized to determine if the pressure pod diaphragm 410 is out of position. Once the standard curve 254, 706 is calculated, for a specific dialysis machine and patient parameters, the pressure pod sensor measurement 704 is compared to the standard curve 706. If the pressure pod measurement 704 is not within a specified range of the standard curve 706, for example plus or minus 15 mmHg as shown by lines 702, 716 or by a specified plus or minus percentage of the standard curve value, the controller 140 may generate an alert, alarm, or warning to alert medical staff that the diaphragm 410 is out of position such that the pressure readings from the device 400 may be inaccurate such that a venous needle dislodgement may occur undetected.

While exemplary embodiments are described above, it is not intended that these embodiments describe all possible forms of the disclosure. Rather, the words used in the specification are words of description rather than limitation, and it is understood that various changes may be made without departing from the spirit and scope of the disclosure. Additionally, the features of various implementing embodiments may be combined to form further embodiments of the disclosure.

What is claimed is:

1. A method of detecting a condition indicative of a dislodged needle in a hemodialysis procedure, comprising the steps of:
   measuring a venous return pressure for a patient undergoing dialysis;
   via a controller, analyzing the venous return pressure and deriving an intravascular blood pressure in proximity to a location of needle insertion into the patient;
   via the controller, calculating a lower limit as a function of the intravascular blood pressure;
   via the controller, calculating an average of the venous return pressure during a predetermined time window; and
   via the controller, comparing the average to the lower limit, and if the average is within a specified range of the lower limit, determining with the controller that a condition indicative of a dislodged needle is present.

2. The method of claim 1 further comprising, in response to determining that the condition is present, activating an alert to notify medical personnel.

3. The method of claim 1 further comprising, in response to determining that the condition is present, stopping a blood pump of a hemodialysis machine.

4. The method of claim 3, further comprising: in response to determining that the condition is present and stopping the blood pump, rederiving the intravascular blood pressure using a current venous return pressure and a height of the location of needle insertion relative to a sensor measuring the venous return pressure; and
   in response to the rederived intravascular blood pressure being below a predetermined value, at least one of preventing the machine from being restarted and activating a second alert.

5. The method of claim 1 wherein the intravascular blood pressure comprises a venous access pressure.

6. The method of claim 1 wherein via the controller, the intravascular blood pressure is derived using venous return pressure measured while a blood pump of a hemodialysis machine has a flow rate of zero.

7. The method of claim 1 wherein the specified range is one of a predetermined constant value and a function of the derived intravascular blood pressure.

8. The method of claim 1 wherein the intravascular blood pressure is derived using the measured venous return pressure and a function of a blood flow rate, a hematocrit, and a height of the location of needle insertion relative to a sensor measuring venous return pressure.

9. The method of claim 1 wherein the intravascular blood pressure is derived as a function of the venous return pressure measured when a blood pump of a hemodialysis machine is stopped and a height of the location of needle insertion relative to a sensor measuring venous return pressure.

10. The method of claim 1 further comprising, via the controller, comparing the venous return pressure to a standard, and if the venous return pressure is outside a specified range of the standard, determining with the controller that a condition indicative of a misaligned diaphragm in a pressure sensor is present.

11. The method of claim 10 further comprising, via the controller, calculating the standard as a function of a blood flow rate.

12. The method of claim 1 wherein the predetermined time window is a first predetermined time window such that the average of the venous return pressure is a first average, the method further comprising:
    via the controller, calculating a second average of the venous return pressure over a second predetermined time window, the second predetermined time window occurring prior to the first predetermined time window; and
    wherein, via the controller, the lower limit is calculated as the function of the intravascular blood pressure and the second average.

13. The method of claim 12 wherein a predetermined time interval elapses between the first and second predetermined time windows.

14. The method of claim 13 wherein the first average and the second average are each calculated as moving averages and the first and second time windows are set as fixed time windows relative to a present time of operation of a hemodialysis machine.

15. The method of claim 13 further comprising, using the controller, communicating with a memory system comprising a shift register to calculate the first and second averages.

16. The method of claim 13 using the controller, calculating a rate of change of the venous return pressure as a function of the first average, the second average, and the time interval; and
    using the controller, comparing the rate to a specified rate, and if the rate is outside of a predetermined range of the specified rate, determining with the controller that a condition indicative of a dislodged needle is present.

17. The method of claim 16 wherein the specified rate is one of a predetermined constant value and a function of the derived intravascular blood pressure.

18. The method of claim 1, wherein, via the controller, the lower limit is calculated as the function of the intravascular blood pressure and a standard.

19. The method of claim 18 further comprising, via the controller, determining a standard as a function of a blood flow rate.

20. The method of claim 18 further comprising, via the controller, correcting the venous return pressure using a venous correction factor prior to calculating the average.

21. The method of claim 20 further comprising, via the controller, calculating the venous correction factor as a function of measured venous return pressure, the standard, and a height of the needle insertion relative to a sensor measuring venous return pressure.

22. The method of claim 20 wherein the venous correction factor corrects the venous return pressure for at least one of a variation in a height of the needle insertion relative to a sensor measuring venous return pressure and a drift of the measured venous return pressure over time.

23. The method of claim 20 further comprising, via the controller, continually updating the venous correction factor during the procedure.

24. The method of claim 23, further comprising, via the controller, in response to a predetermined decrease in measured venous return pressure within a predetermined time period, using a previously stored venous correction factor in place of a current venous correction factor to correct the venous return pressure.

25. A device for detecting a condition indicative of a dislodged needle in a hemodialysis procedure comprising:
a controller configured to communicate with a hemodialysis machine, the controller configured to: (i) receive a signal indicative of a venous return pressure measurement for a patient undergoing dialysis, (ii) analyze the measured venous return pressure and derive an intravascular blood pressure in proximity to a location of needle insertion into the patient, (iii) calculate a lower limit as a function of the intravascular blood pressure, (iv) calculate an average of the venous return pressure during a predetermined time window, (v) compare the average to the lower limit, and if the average is within a specified range of the lower limit, determine that a condition indicative of at least a partially dislodged needle is present, and (vi) provide at least one of a first signal configured to activate an alert to notify medical personnel and a second signal configured to stop a blood pump of the hemodialysis machine.

26. A method of detecting a condition indicative of a dislodged needle in a medical procedure with a system having an extracorporeal fluid circuit receiving and returning blood to a patient, comprising the steps of:
measuring a first fluid pressure in the circuit upstream of a location of needle insertion into the patient;
via a controller, analyzing the first fluid pressure and deriving a second fluid pressure in proximity to the location of needle insertion into the patient;
via the controller, calculating a lower limit as a function of the second fluid pressure;
via the controller, calculating an average of the first fluid pressure over a predetermined time interval; and
if the average is within a specified range of the lower limit, determining via the controller that a condition indicative of a dislodged needle is present.

* * * * *